(12) United States Patent
Burk et al.

(10) Patent No.: US 7,557,095 B2
(45) Date of Patent: Jul. 7, 2009

(54) THERAPEUTIC COMPOUNDS

(75) Inventors: Robert M. Burk, Laguna Beach, CA (US); David W. Old, Irvine, CA (US); Todd Gac, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 21 days.

(21) Appl. No.: 11/745,317

(22) Filed: May 7, 2007

(65) Prior Publication Data

US 2007/0265321 A1 Nov. 15, 2007

Related U.S. Application Data

(60) Provisional application No. 60/747,115, filed on May 12, 2006.

(51) Int. Cl.
| | |
|---|---|
| A61K 31/67 | (2006.01) |
| A61K 31/425 | (2006.01) |
| A61K 31/426 | (2006.01) |
| A61K 31/427 | (2006.01) |
| C07D 275/02 | (2006.01) |
| C07D 275/03 | (2006.01) |
| C07D 277/22 | (2006.01) |
| C07D 277/32 | (2006.01) |
| C07D 417/06 | (2006.01) |
| C07D 417/12 | (2006.01) |
| C07F 9/38 | (2006.01) |

(52) U.S. Cl. ............. 514/92; 514/365; 514/369; 514/372; 548/112; 548/119; 548/206; 548/213; 548/214; 548/182; 548/186; 548/202; 548/203

(58) Field of Classification Search ............. 548/213, 548/250, 214, 112, 119, 206, 182, 186, 202, 548/203; 514/381, 372, 382, 92, 365, 369
See application file for complete search history.

(56) References Cited

U.S. PATENT DOCUMENTS

| 5,902,726 | A | 5/1999 | Kliewer et al. |
| 6,476,064 | B1 | 11/2002 | Old et al. |
| 6,927,216 | B2 * | 8/2005 | Cherney et al. .......... 514/222.2 |
| 2002/0032222 | A1 | 3/2002 | Malamas et al. |

FOREIGN PATENT DOCUMENTS

| WO | WO95/29904 | 11/1995 |
| WO | WO97/03973 | 2/1997 |

OTHER PUBLICATIONS

Mandred E. Wolff, Burger's Medicinal Chemistry and Drug Discovery, 1994, Wiley-Interscience, Fifth Edition, vol. I: Principles and Practice, pp. 975-977.*
Dragoli, et al., "Parallel Synthesis of Prostaglandin $E_1$ Analogues," J. Comb. Chem., 1999, 1, pp. 534-539.
Baxter, et al., "Synthesis and Use of 7-Substituted Norbornadienes + for the Preparation of Prostaglandins and Prostanoids," J. Chem. SOc. Perkin Trans., I, 1986, pp. 889-900.

* cited by examiner

*Primary Examiner*—Kamal A Saeed
*Assistant Examiner*—Kristin Bianchi
(74) *Attorney, Agent, or Firm*—Allergan, Inc.; Kevin Forrestal

(57) ABSTRACT

Disclosed herein is a compound having a structure

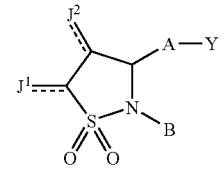

or a pharmaceutically acceptable salt thereof, or a prodrug thereof. Therapeutic methods, compositions, and medicaments related thereto are also disclosed.

21 Claims, No Drawings

THERAPEUTIC COMPOUNDS

RELATED APPLICATION

This application claims the benefit of U.S. Provisional Application Ser. No. 60/747,115, filed May 12, 2006, which is hereby incorporated by reference in its entirety.

BACKGROUND

Ocular hypotensive agents are useful in the treatment of a number of various ocular hypertensive conditions, such as post-surgical and post-laser trabeculectomy ocular hypertensive episodes, glaucoma, and as presurgical adjuncts. Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain eicosanoids and their derivatives are currently commercially available for use in glaucoma management. Eicosanoids and derivatives include numerous biologically important compounds such as prostaglandins and their derivatives. Prostaglandins can be described as derivatives of prostanoic acid which have the following structural formula:

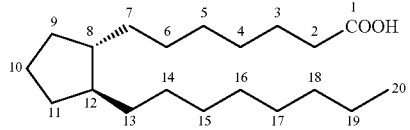

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

DESCRIPTION OF THE INVENTION

Disclosed herein is a compound having a structure

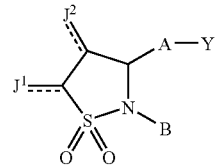

or a pharmaceutically acceptable salt thereof, or a prodrug thereof;

wherein a dashed line represents the presence or absence of a bond;

Y is an organic acid functional group, or an amide or ester thereof comprising up to 14 carbon atoms; or Y is hydroxymethyl or an ether thereof comprising up to 14 carbon atoms; or Y is a tetrazolyl functional group;

A is —$(CH_2)_6$—, cis —$CH_2CH$=$CH$—$(CH_2)_3$—, or —$CH_2C$≡$C$—$(CH_2)_3$—, wherein 1 or 2 carbon atoms may be replaced by S or O; or A is —$(CH_2)_m$—Ar—$(CH_2)_o$— wherein Ar is interarylene or heterointerarylene, the sum of m and o is 1, 2, 3, or 4, and wherein one $CH_2$ may be replaced by S or O;

$J^1$ and $J^2$ are independently H; O; OH; O-alkyl having 1, 2, 3, 4, 5 or 6 carbon atoms; alkyl having 1, 2, 3, 4, 5, or 6 carbon atoms;

F; Cl; Br; I; CN; or $CF_3$; and

B is substituted aryl or substituted heteroaryl.

Also disclosed herein is a carboxylic acid or a bioisostere thereof, said carboxylic acid having a structure

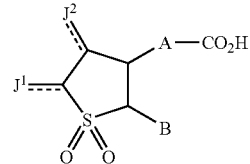

or a pharmaceutically acceptable salt thereof, or a prodrug thereof;

wherein a dashed line represents the presence or absence of a bond;

A is —$(CH_2)_6$—, cis —$CH_2CH$=$CH$—$(CH_2)_3$—, or —$CH_2C$≡$C$—$(CH_2)_3$—, wherein 1 or 2 carbon atoms may be replaced by S or O; or A is —$(CH_2)_m$—Ar—$(CH_2)_o$— wherein Ar is interarylene or heterointerarylene, the sum of m and o is 1, 2, 3, or 4, and wherein one $CH_2$ may be replaced by S or O;

$J^1$ and $J^2$ are independently H; O; OH; O-alkyl having 1, 2, 3, 4, 5 or 6 carbon atoms; alkyl having 1, 2, 3, 4, 5, or 6 carbon atoms;

F; Cl; Br; I; CN; or $CF_3$; and

B is substituted aryl or substituted heteroaryl.

"Bioisosteres are substituents or groups that have chemical or physical similarities, and which produce broadly similar biological properties." Silverman, Richard B., *The Organic Chemistry of Drug Design and Drug Action*, 2nd Edition, Amsterdam: Elsevier Academic Press, 2004, p. 29.

While not intending to be limiting, organic acid functional groups are bioisoteres of carboxylic acids. An organic acid functional group is an acidic functional group on an organic molecule. While not intending to be limiting, organic acid functional groups may comprise an oxide of carbon, sulfur, or phosphorous. Thus, while not intending to limit the scope of the invention in any way, in certain compounds Y is a carboxylic acid, sulfonic acid, or phosphonic acid functional group.

Additionally, an amide or ester of one of the organic acids mentioned above comprising up to 14 carbon atoms is also contemplated. In an ester, a hydrocarbyl moiety replaces a hydrogen atom of an acid such as in a carboxylic acid ester, e.g. $CO_2Me$, $CO_2Et$, etc.

In an amide, an amine group replaces an OH of the acid. Examples of amides include $CON(R^2)_2$, $CON(OR^2)R^2$, $CON(CH_2CH_2OH)_2$, and $CONH(CH_2CH_2OH)$ where $R^2$ is independently H, $C_1$-$C_6$ alkyl, phenyl, or biphenyl. Moieties such as $CONHSO_2R^2$ are also amides of the carboxylic acid notwithstanding the fact that they may also be considered to be amides of the sulfonic acid $R^2$—$SO_3H$. The following amides are also specifically contemplated, $CONSO_2$-biphenyl, $CONSO_2$-phenyl, $CONSO_2$-heteroaryl, and $CONSO_2$-naphthyl. The biphenyl, phenyl, heteroaryl, or naphthyl may be substituted or unsubstituted.

Han et. al. (Biorganic & Medicinal Chemistry Letters 15 (2005) 3487-3490) has recently shown that the groups shown below are suitable bioisosteres for a carboxylic acid. The activity of compounds with these groups in inhibiting HCV NS3 protease was comparable to or superior to similar compounds where the group is replaced by $CO_2H$. Thus, Y could be any group depicted below.

Carboxylic Acid Bioisosteres According to Han et. al.

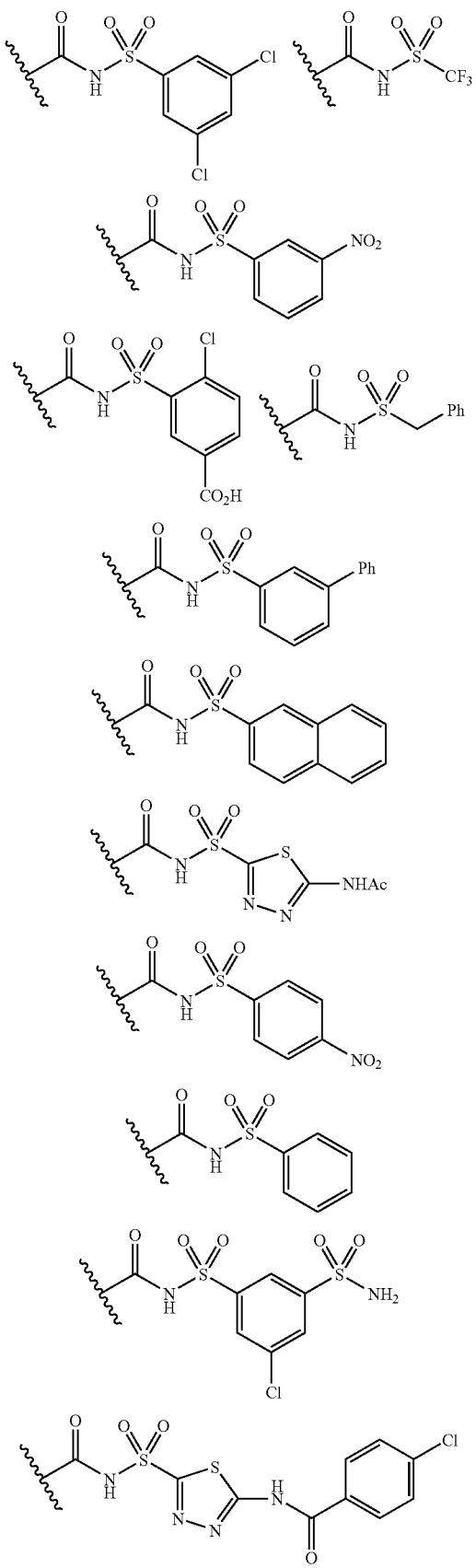

-continued

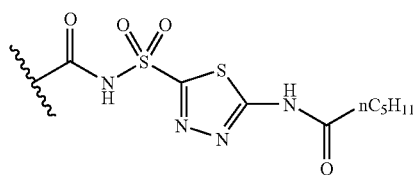

While not intending to limit the scope of the invention in any way, Y may also be hydroxymethyl or an ether thereof comprising up to 14 carbon atoms. An ether is a functional group wherein a hydrogen of an hydroxyl is replaced by carbon, e.g., Y is $CH_2OCH_3$, $CH_2OCH_2CH_3$, etc. These groups are also bioisosteres of a carboxylic acid.

"Up to 14 carbon atoms" means that the entire Y moiety, including the carbonyl carbon of a carboxylic acid ester or amide, and both carbon atoms in the —$CH_2O$—C of an ether has 0, 1, 2, 3, 4, 5, 6, 7, 8, 9, 10, 11, 12, 13, or 14 carbon atoms.

Finally, while not intending to limit the scope of the invention in any way, Y may be a tetrazolyl functional group.

While not intending to be limiting, examples of compounds having the identified Y are depicted below. In these examples R is H or hydrocarbyl, subject to the constraints defined herein. Each structure below represents a specific embodiment which is individually contemplated, as well as pharmaceutically acceptable salts and prodrugs of compounds which are represented by the structures. However, other examples are possible which may not fall within the scope of the structures shown below.

Y is tetrazolyl.

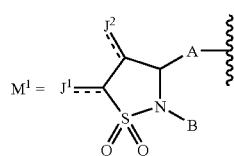

$M^1 =$ 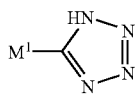

| Organic Acids | Esters | Amides |
|---|---|---|
| $M^1$—$CO_2H$ | $M^1$—$CO_2R$ | $M^1$—$CO_2NR_2$ |
| Carboxylic Acid | Carboxylic Acid Ester | Carboxylic Acid Amide |
| $M^1$—$P(O)(OH)_2$ | $M^1$—$P(O)(OH)R$ | $M^1$—$P(O)(OH)NR_2$ |
| Phosponic Acid | Phosphonic Acid Ester | Phosphonic Acid Amide |
| $M^1$—$SO_3H$ | $M^1$—$SO_3R$ | $M^1$—$SO_3NR_2$ |
| Sulfonic Acid | Sulfonic Acid Ester | Sulfonic Acid Amide |
| $M^1$—$CH_2OH$ | $M^1$—$CH_2OR$ | |
| Y is hydroxymethyl | Ether | |

A tetrazolyl functional group is another bioisostere of a carboxylic acid. An unsubstituted tetrazolyl functional group has two tautomeric forms, which can rapidly interconvert in aqueous or biological media, and are thus equivalent to one another. These tautomers are shown below.

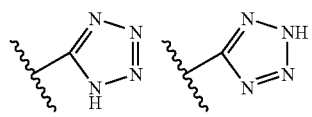

Additionally, if $R^2$ is $C_1$-$C_6$ alkyl, phenyl, or biphenyl, other isomeric forms of the tetrazolyl functional group such as the one shown below are also possible, unsubstituted and hydrocarbyl substituted tetrazolyl up to $C_{12}$ are considered to be within the scope of the term "tetrazolyl."

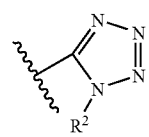

While not intending to limit the scope of the invention in any way, in one embodiment, Y is $CO_2R^2$, $CON(R^2)_2$, $CON(OR^2)R^2$, $CON(CH_2CH_2OH)_2$, $CONH(CH_2CH_2OH)$, $CH_2OH$, $P(O)(OH)_2$, $CONHSO_2R^2$, $SO_2N(R^2)_2$, $SO_2NHR^2$,

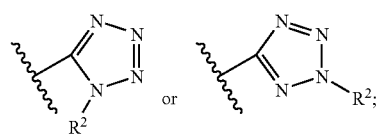

wherein $R^2$ is independently H, $C_1$-$C_6$ alkyl, unsubstituted phenyl, or unsubstituted biphenyl.

According to Silverman (p. 30), the moieties shown below are also bioisosteres of a carboxylic acid.

Carboxylic Acid Bioisosteres According to Silverman

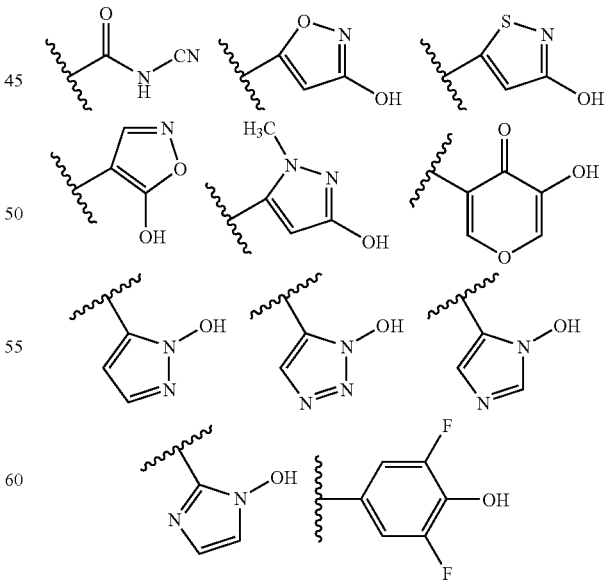

Orlek et al. (*J. Med. Chem.* 1991, 34, 2726-2735) described oxadiazoles as suitable bioisosteres for a carboxylic acid.

These ester replacements were shown to be potent muscarinic agonists having improved metabolic stability. Oxadiazoles were also described by Anderson et al. (Eur. J. Med. Chem. 1996, 31, 417-425) as carboxamide replacements having improved in vivo efficacy at the benzodiazepine receptor.

Carboxylic Acid Bioisosteres According to Orlek et. al.

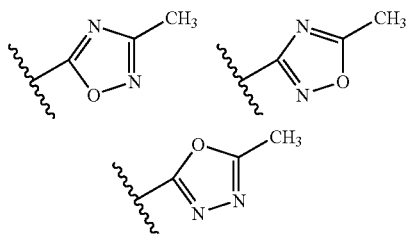

Kohara et al. (J. Med. Chem. 1996, 39, 5228-5235) described acidic heterocycles as suitable bioisosteres for a tetrazole. These carboxylic acid replacements were shown to be potent angiotensin II receptor antagonists having improved metabolic stability.

Tetrazole Bioisosteres According to Kohara et. al.

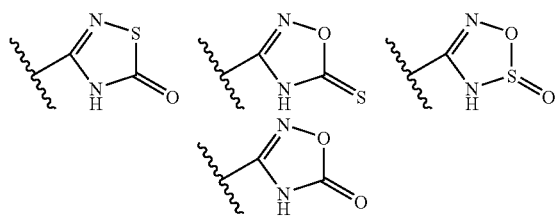

Drysdale et al. (J. Med. Chem. 1992, 35, 2573-2581) have described carboxylic acid mimics of non-peptide CCK-B receptor antagonists. The binding affinities of many of the bioisosteres are similar to the parent carboxylic acid.

Carboxylic Acid Bioisosteres According to Drysdale et. al.

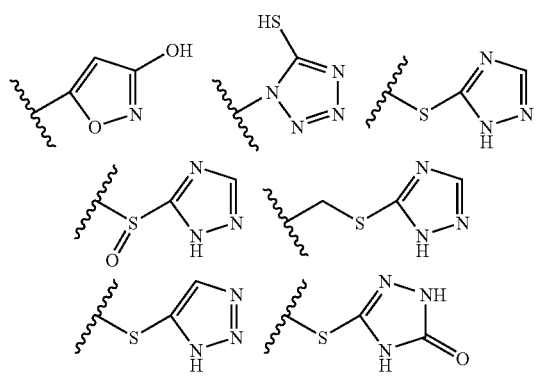

In relation to the identity of A disclosed in the chemical structures presented herein, A is —(CH$_2$)$_6$—, cis —CH$_2$CH═CH—(CH$_2$)$_3$—, or —CH$_2$C≡C—(CH$_2$)$_3$—, wherein 1 or 2 carbon atoms may be replaced with S or O; or A is —(CH$_2$)$_m$—Ar—(CH$_2$)$_o$— wherein Ar is interarylene or heterointerarylene, the sum of m and o is 1, 2, 3, or 4, and wherein one CH$_2$ may be replaced with S or O.

While not intending to be limiting, A may be —(CH$_2$)$_6$—, cis —CH$_2$CH═CH—(CH$_2$)$_3$—, or —CH$_2$C≡C—(CH$_2$)$_3$—.

Alternatively, A may be a group which is related to one of these three moieties in that any carbon is replaced with S or O. For example, while not intending to limit the scope of the invention in any way, A may be a moiety where S replaces one or two carbon atoms such as one of the following or the like.

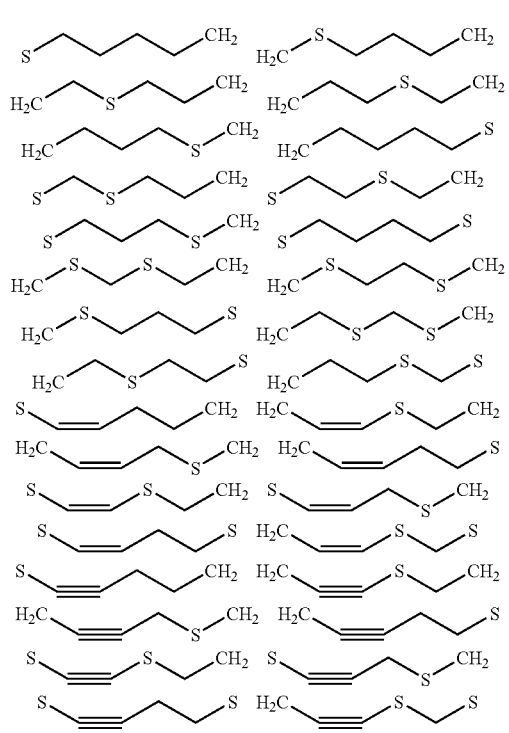

Alternatively, while not intending to limit the scope of the invention in any way, A may be a moiety where O replaces one or two carbon atoms such as one of the following or the like.

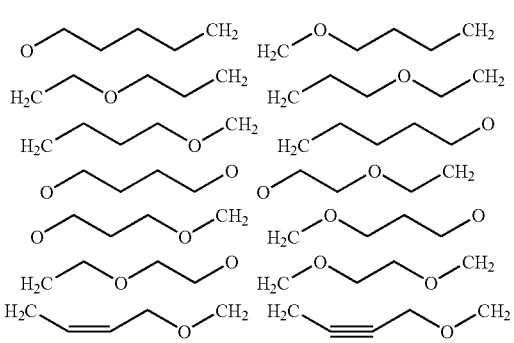

Alternatively, while not intending to limit the scope of the invention in any way, A may have an O replacing one carbon atom and an S replacing another carbon atom, such as one of the following or the like.

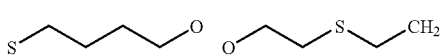

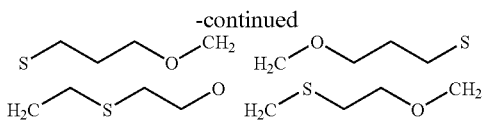

Alternatively, while not intending to limit the scope of the invention in any way, in certain embodiments A is —(CH$_2$)$_m$—Ar—(CH$_2$)$_o$— wherein Ar is interarylene or heterointerarylene, the sum of m and o is 1, 2, 3, or 4, and wherein one CH$_2$ may be replaced with S or O. In other words, while not intending to limit the scope of the invention in any way, in one embodiment A comprises 1, 2, 3, or 4 CH$_2$ moieties and Ar, e.g. —CH$_2$—Ar—, —(CH$_2$)$_2$—Ar—, —CH$_2$—Ar—CH$_2$—, —CH$_2$Ar—(CH$_2$)$_2$—, —(CH$_2$)$_2$—Ar—(CH$_2$)$_2$—, and the like;

in another embodiment A comprises: O; 0, 1, 2, or 3 CH$_2$ moieties; and Ar, e.g., —O—Ar—, Ar—CH$_2$—O—, —O—Ar—(CH$_2$)$_2$—, —O—CH$_2$—Ar—, —O—CH$_2$—Ar—(CH$_2$)$_2$, and the like; or in another embodiment A comprises: S; 0, 1, 2, or 3 CH$_2$ moieties; and Ar, e.g., —S—Ar—, Ar—CH$_2$—S—, —S—Ar—(CH$_2$)$_2$—, —S—CH$_2$—Ar—, —S—CH$_2$—Ar—(CH$_2$)$_2$, —(CH$_2$)$_2$—S—Ar, and the like.

In another embodiment, the sum of m and o is 2, 3, or 4 wherein one CH$_2$ may be replaced with S or O.

In another embodiment, the sum of m and o is 3 wherein one CH$_2$ may be replaced with S or O.

In another embodiment, the sum of m and o is 2 wherein one CH$_2$ may be replaced with S or O.

In another embodiment, the sum of m and o is 4 wherein one CH$_2$ may be replaced with S or O.

Interarylene or heterointerarylene refers to an aryl ring or ring system or a heteroaryl ring or ring system which connects two other parts of a molecule, i.e. the two parts are bonded to the ring in two distinct ring positions. Interarylene or heterointerarylene may be substituted or unsubstituted. Unsubstituted interarylene or heterointerarylene has no substituents other than the two parts of the molecule it connects. Substituted interarylene or heterointerarylene has substituents in addition to the two parts of the molecule it connects.

In one embodiment, Ar is substituted or unsubstituted interphenylene, interthienylene, interfurylene, interpyridinylene, interoxazolylene, and interthiazolylene. In another embodiment Ar is interphenylene (Ph). In another embodiment A is —(CH$_2$)$_2$-Ph-. While not intending to limit scope of the invention in any way, substituents may have 4 or less heavy atoms, wherein the heavy atoms are C, N, O, S, P, F, Cl, Br, and/or I in any stable combination. Any number of hydrogen atoms required for a particular substituent will also be included. A substituent must be stable enough for the compound to be useful as described herein. In addition to the atoms listed above, a substituent may also have a metal cation or any other stable cation having an atom not listed above if the substituent is acidic and the salt form is stable. For example, —OH may form an —O—Na$^+$ salt or CO$_2$H may form a CO$_2$—K$^+$ salt. Any cation of the salt is not counted in the "4 or less heavy atoms." Thus, the substituent may be hydrocarbyl having up to 4 carbon atoms, including alkyl up to C$_4$, alkenyl, alkynyl, and the like;

hydrocarbyloxy up to C$_3$;

organic acid such as CO$_2$H, SO$_3$H, P(O)(OH)$_2$, and the like, and salts thereof;

CF$_3$;

halo, such as F, Cl, or Br;

hydroxyl;

NH$_2$ and alkylamine functional groups up to C$_3$;

other N or S containing substituents such as CN, NO$_2$, and the like;

and the like.

In one embodiment A is —(CH$_2$)$_m$-Ph-(CH$_2$)$_o$— wherein the sum of m and o is 1, 2, or 3, and wherein one CH$_2$ may be replaced with S or O.

In another embodiment A is —CH$_2$—Ar—OCH$_2$—. In another embodiment A is —CH$_2$-Ph-OCH$_2$—. In another embodiment, Ph is attached at the 1 and 3 positions, otherwise known as m-interphenylene, such as when A has the structure shown below.

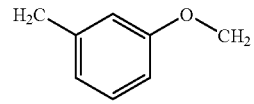

In another embodiment A is —(CH$_2$)$_6$—, cis —CH$_2$CH═CH—(CH$_2$)$_3$—, or —CH$_2$C≡C—(CH$_2$)$_3$—, wherein 1 or 2 carbon atoms may be replaced with S or O; or A is —(CH$_2$)$_2$-Ph- wherein one CH$_2$ may be replaced with S or O.

In another embodiment A is —(CH$_2$)$_6$—, cis —CH$_2$CH═CH—(CH$_2$)$_3$—, or —CH$_2$C≡C—(CH$_2$)$_3$—, wherein 1 or 2 carbon atoms may be replaced with S or O; or A is —(CH$_2$)$_2$-Ph-.

In other embodiments, A has one of the following structures, where Y is attached to the aromatic or heteroaromatic ring.

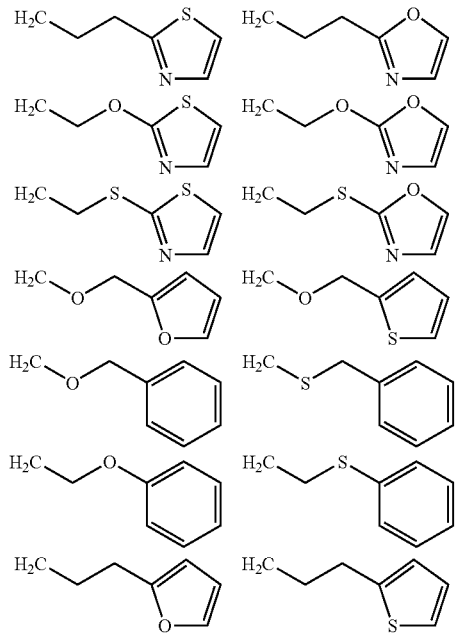

In another embodiment A is —CH$_2$OCH$_2$Ar.
In another embodiment A is —CH$_2$SCH$_2$Ar.
In another embodiment A is —(CH$_2$)$_3$Ar.
In another embodiment A is —CH$_2$O(CH$_2$)$_4$.
In another embodiment A is —CH$_2$S(CH$_2$)$_4$.
In another embodiment A is —(CH$_2$)$_6$—.
In another embodiment A is cis —CH$_2$CH═CH—(CH$_2$)$_3$—.
In another embodiment A is —CH$_2$C≡C—(CH$_2$)$_3$—.
In another embodiment A is —S(CH$_2$)$_3$S(CH$_2$)$_2$—.
In another embodiment A is —(CH$_2$)$_4$OCH$_2$—.

In another embodiment A is cis —CH$_2$CH=CH—CH$_2$OCH$_2$—.
In another embodiment A is —CH$_2$CH≡CH—CH$_2$OCH$_2$—.
In another embodiment A is —(CH$_2$)$_2$S(CH$_2$)$_3$—.
In another embodiment A is —CH$_2$-Ph-OCH$_2$—, wherein Ph is interphenylene.
In another embodiment A is —CH$_2$-mPh-OCH$_2$—, wherein mPh is m-interphenylene.
In another embodiment A is —CH$_2$—O—(CH$_2$)$_4$—.
In another embodiment A is —CH$_2$—O—CH$_2$—Ar—, wherein Ar is 2,5-interthienylene.
In another embodiment A is —CH$_2$—O—CH$_2$—Ar—, wherein Ar is 2,5-interfurylene.
In another embodiment A is (3-methylphenoxy)methyl.
In another embodiment A is (4-but-2-ynyloxy)methyl.
In another embodiment A is 2-(2-ethylthio)thiazol-4-yl.
In another embodiment A is 2-(3-propyl)thiazol-5-yl.
In another embodiment A is 3-methoxymethyl)phenyl.
In another embodiment A is 3-(3-propylphenyl.
In another embodiment A is 3-methylphenethyl.
In another embodiment A is 4-(2-ethyl)phenyl.
In another embodiment A is 4-phenethyl.
In another embodiment A is 4-methoxybutyl.
In another embodiment A is 5-(methoxymethyl)furan-2-yl.
In another embodiment A is 5-(methoxymethyl)thiophen-2-yl.
In another embodiment A is 5-(3-propyl)furan-2-yl.
In another embodiment A is 5-(3-propyl)thiophene-2-yl.
In another embodiment A is 6-hexyl.
In another embodiment A is (Z)-6-hex-4-enyl.
In another embodiment, A is —(CH$_2$)$_m$—Ar—(CH$_2$)$_o$— wherein Ar is interarylene or heterointerarylene, the sum of m and o is 1, 2, 3, or 4, and wherein one CH$_2$ may be replaced by S or O.
In another embodiment, A is —(CH$_2$)$_3$Ar—, —O(CH$_2$)$_2$Ar—, —CH$_2$OCH$_2$Ar—, —(CH$_2$)$_2$OAr, —O(CH$_2$)$_2$Ar—, —CH$_2$OCH$_2$Ar—, or —(CH$_2$)$_2$OAr, wherein Ar is monocyclic interheteroarylene.
In another embodiment, Ar is interthienylene.
In another embodiment, Ar is interthiazolylene.
In another embodiment, Ar is interoxazolylene.
Compounds according to the each of the structures depicted below, and pharmaceutically acceptable salts thereof, and prodrugs thereof, are contemplated as individual embodiments. In other words, each structure represents a different embodiment.

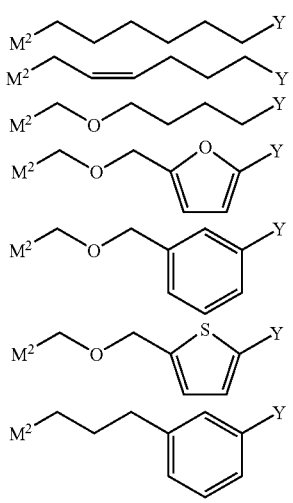

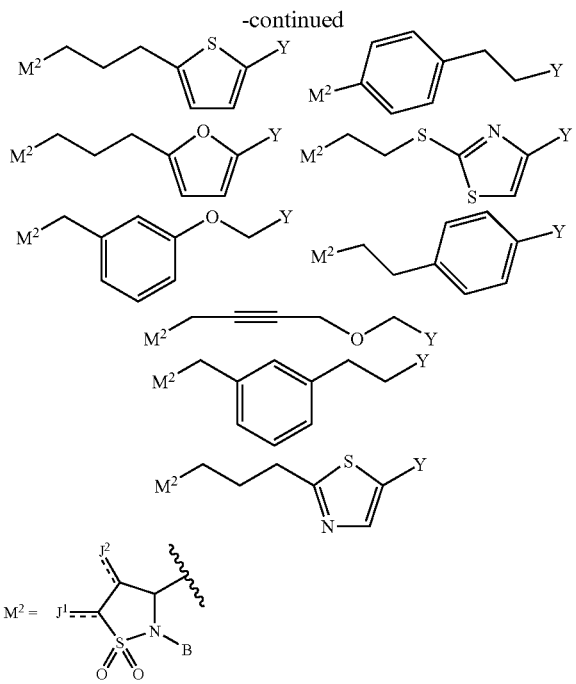

$J^1$ and $J^2$ are independently H; O; OH; O-alkyl having 1, 2, 3, 4, 5 or 6 carbon atoms; alkyl having 1, 2, 3, 4, 5, or 6 carbon atoms; F; Cl; Br; I; CN; or CF$_3$. Thus, each structure depicted below represents a compound embodiment which is individually contemplated. Pharmaceutically acceptable salts and prodrugs of compounds according to the structures below are also contemplated.

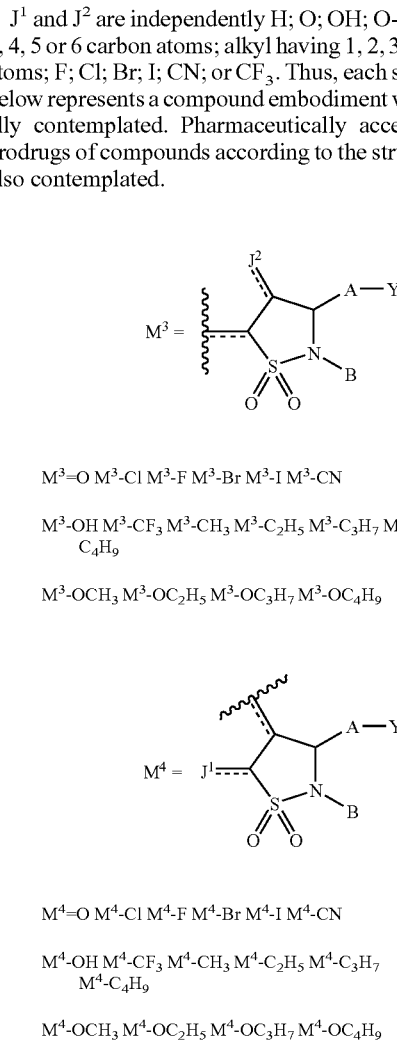

M$^3$=O M$^3$-Cl M$^3$-F M$^3$-Br M$^3$-I M$^3$-CN

M$^3$-OH M$^3$-CF$_3$ M$^3$-CH$_3$ M$^3$-C$_2$H$_5$ M$^3$-C$_3$H$_7$ M$^3$-C$_4$H$_9$

M$^3$-OCH$_3$ M$^3$-OC$_2$H$_5$ M$^3$-OC$_3$H$_7$ M$^3$-OC$_4$H$_9$

M$^4$=O M$^4$-Cl M$^4$-F M$^4$-Br M$^4$-I M$^4$-CN

M$^4$-OH M$^4$-CF$_3$ M$^4$-CH$_3$ M$^4$-C$_2$H$_5$ M$^4$-C$_3$H$_7$ M$^4$-C$_4$H$_9$

M$^4$-OCH$_3$ M$^4$-OC$_2$H$_5$ M$^4$-OC$_3$H$_7$ M$^4$-OC$_4$H$_9$

Aryl is an aromatic ring or ring system such as phenyl, naphthyl, biphenyl, and the like.

Heteroaryl is aryl having one or more N, O, or S atoms in the ring, i.e. one or more ring carbons are substituted by N, O, and/or S. While not intending to be limiting, examples of heteroaryl include thienyl, pyridinyl, furyl, benzothienyl, benzofuryl, imidizololyl, indolyl, and the like.

A substituent of aryl or heteroaryl may have up to 20 non-hydrogen atoms each in any stable combination and as many hydrogen atoms as necessary, wherein the non-hydrogen atoms are C, N, O, S, P, F, Cl, Br, and/or I in any stable combination. However, the total number of non-hydrogen atoms on all of the substituents combined must also be 20 or less. A substituent must be sufficiently stable for the compound to be useful as described herein. In addition to the atoms listed above, a substituent may also have a metal cation or other stable cation having an atom not listed above if the substituent is acidic and the salt form is stable. For example, —OH may form an —O—Na$^+$ salt or CO$_2$H may form a CO$_2$—K$^+$ salt. Thus, while not intending to limit the scope of the invention in any way, a substituent may be:

hydrocarbyl, i.e. a moiety consisting of only carbon and hydrogen such as alkyl, alkenyl, alkynyl, and the like, including linear, branched or cyclic hydrocarbyl, and combinations thereof;

hydrocarbyloxy, meaning O-hydrocarbyl such as OCH$_3$, OCH$_2$CH$_3$, O-cyclohexyl, etc, up to 19 carbon atoms;

other ether substituents such as CH$_2$OCH$_3$, (CH$_2$)$_2$OCH(CH$_3$)$_2$, and the like;

thioether substituents including S-hydrocarbyl and other thioether substituents;

hydroxyhydrocarbyl, meaning hydrocarbyl-OH such as CH$_2$OH, C(CH$_3$)$_2$OH, etc, up to 19 carbon atoms;

nitrogen substituents such as NO$_2$, CN, and the like, including amino, such as NH$_2$, NH(CH$_2$CH$_2$OH), NHCH$_3$, and the like;

carbonyl substituents, such as CO$_2$H, ester, amide, and the like;

halogen, such as chloro, fluoro, bromo, and the like fluorocarbyl, such as CF$_3$, CF$_2$CF$_3$, etc.;

phosphorous substituents, such as PO$_3^{2-}$, and the like;

sulfur substituents, including S-hydrocarbyl, SH, SO$_3$H, SO$_2$-hydrocarbyl, SO$_3$-hydrocarbyl, and the like.

Substituted aryl or heteroaryl may have as many substituents as the ring or ring system will bear, and the substituents may be the same or different. Thus, for example, an aryl ring or a heteroaryl ring may be substituted with chloro and methyl; methyl, OH, and F; CN, NO$_2$, and ethyl; and the like including any conceivable substituent or combination of substituent possible in light of this disclosure.

Substituted aryl or substituted heteroaryl also includes a bicyclic or polycyclic ring system wherein one or more rings are aromatic and one or more rings are not. For example, indanonyl, indanyl, indanolyl, tetralonyl, and the like are substituted aryl. For this type of polycyclic ring system, an aromatic or heteroaromatic ring, not a non-aromatic ring, must be attached to the remainder of the molecule, i.e. the part of the molecule that is not B. In other words, in any structure depicting —B herein, where — is a bond, the bond is a direct bond to an aromatic ring.

In one embodiment, B is substituted aryl or heteroaryl.

In another embodiment B is substituted phenyl.

In another embodiment B has no halogen atoms.

In another embodiment B is 4-(1-hydroxy-2,2-dimethylpropyl)phenyl.

In another embodiment B is 4-(1-hydroxy-2-methylpan-2-yl)phenyl.

In another embodiment B is 4-(1-hydroxy-2-methylpropyl)phenyl.

In another embodiment B is 4-(1-hydroxybutyl)phenyl.

In another embodiment B is 4-(1-hydroxyheptyl)phenyl.

In another embodiment B is 4-(1-hydroxyhexyl)phenyl.

In another embodiment B is 4-(1-hydroxypentyl)phenyl.

In another embodiment B is 4-(1-hydroxypropyl)phenyl.

In another embodiment B is 4-(3-hydroxy-2-methylheptan-2-yl)phenyl.

In another embodiment B is 4-(3-hydroxy-2-methyloctan-2-yl)phenyl.

In another embodiment B is 1-hydroxy-2,3-dihydro-1H-inden-5-yl.

In another embodiment B is 2,3-dihydro-1H-inden-5-yl.

In another embodiment B is 3-(hydroxy(1-propylcyclobutyl)methyl)phenyl.

In another embodiment B is 4-(1-hydroxy-5,5-dimethylhexyl)phenyl.

In another embodiment B is 4-(hydroxy(1-propylcyclobutyl)methyl)phenyl.

In another embodiment B is 4-tert-butylphenyl.

In another embodiment B is 4-hexylphenyl.

In another embodiment B is 4-(1-hydroxy-2-phenylethyl)phenyl.

In another embodiment B is 4-(1-hydroxy-3-phenylpropyl)phenyl.

In another embodiment B is 4-(1-hydroxycyclobutyl)phenyl.

In another embodiment B is 4-(2-cyclohexyl-1-hydroxyethyl)phenyl.

In another embodiment B is 4-(3-cyclohexyl-1-hydroxypropyl)phenyl.

In another embodiment B is 4-(cyclohexyl(hydroxy)methyl)phenyl.

In another embodiment B is 4-(cyclohexylmethyl)phenyl.

In another embodiment B is 4-(hydroxy(phenyl)methyl)phenyl.

Another embodiment is a compound according to the structure

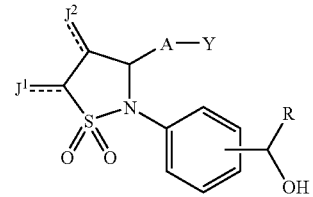

or a pharmaceutical salt thereof, or a prodrug thereof, wherein R is hydrogen or C$_{1-10}$ hydrocarbyl.

Another embodiment is a compound according to the structure

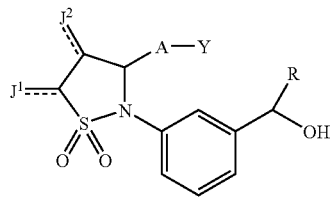

or a pharmaceutical salt thereof, or a prodrug thereof, wherein R is hydrogen or C$_{1-10}$ hydrocarbyl.

Another embodiment is a compound according to the structure

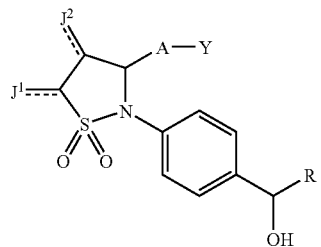

or a pharmaceutical salt thereof, or a prodrug thereof, wherein R is hydrogen or $C_{1-10}$ hydrocarbyl.

Another embodiment is a compound according to the structure

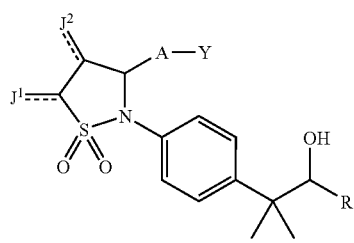

"C1-10" hydrocarbyl is hydrocarbyl having 1, 2, 3, 4, 5, 6, 7, 8, 9, or 10 carbon atoms.

Hydrocarbyl is a moiety consisting of only carbon and hydrogen, and includes, but is not limited to alkyl, alkenyl, alkynyl, and the like, and in some cases aryl, and combinations thereof.

Alkyl is hydrocarbyl having no double or triple bonds including:

linear alkyl such as methyl, ethyl, propyl, n-butyl, n-pentyl, n-hexyl, and the like;

branched alkyl such as isopropyl, branched butyl isomers (i.e. sec-butyl, tert-butyl, etc), branched pentyl isomers (i.e. isopentyl, etc), branched hexyl isomers, and higher branched alkyl fragments;

cycloalkyl such as cyclopropyl, cyclobutyl, cyclopentyl, cyclohexyl, cycloheptyl, etc.; and alkyl fragments consisting of both cyclic and noncyclic components, whether linear or branched, which may be attached to the remainder of the molecule at any available position including terminal, internal, or ring carbon atoms.

Alkenyl is hydrocarbyl having one or more double bonds including linear alkenyl, branched alkenyl, cyclic alkenyl, and combinations thereof in analogy to alkyl.

Alkynyl is hydrocarbyl having one or more triple bonds including linear alkynyl, branched alkynyl, cyclic alkynyl and combinations thereof in analogy to alkyl.

Aryl is an unsubstituted or substituted aromatic ring or ring system such as phenyl, naphthyl, biphenyl, and the like. Aryl may or may not be hydrocarbyl, depending upon whether it has substituents with heteroatoms.

Arylalkyl is alkyl which is substituted with aryl. In other words alkyl connects aryl to the remaining part of the molecule.

Examples are —$CH_2$-Phenyl, —$CH_2$—$CH_2$-Phenyl, and the like. Arylalkyl may or may not be hydrocarbyl, depending upon whether the aryl portion has substituents with heteroatoms.

Unconjugated dienes or polyenes have one or more double bonds which are not conjugated. They may be linear, branched, or cyclic, or a combination thereof.

Combinations of the above are also possible.

Thus, each of the structures below is contemplated. These structures, or pharmaceutically acceptable salts thereof, or prodrugs thereof, individually represent a compound which is an embodiment contemplated herein. In other words, each structure represents a different embodiment.

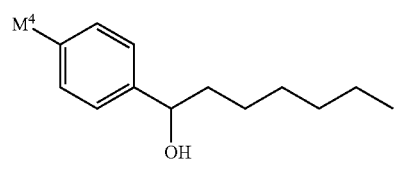

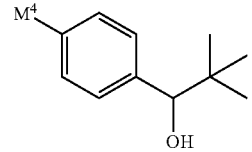

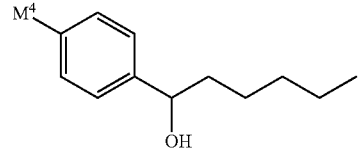

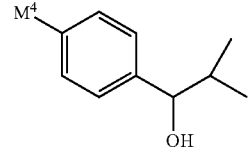

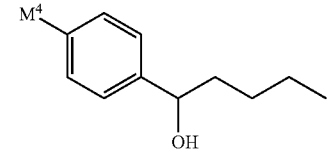

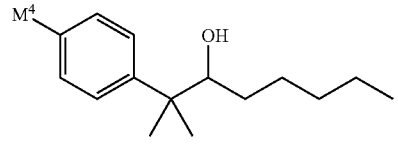

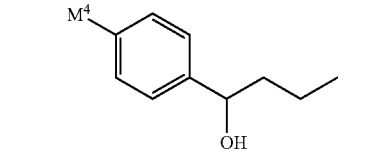

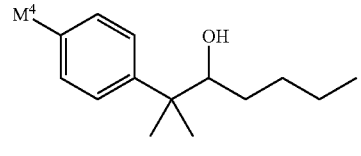

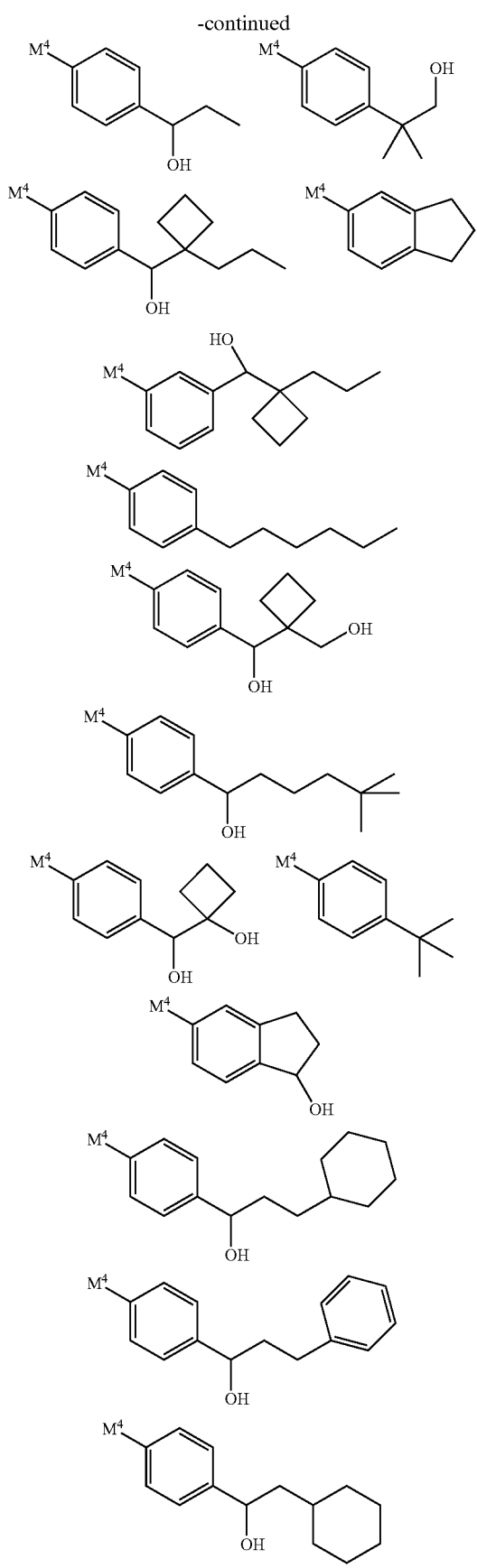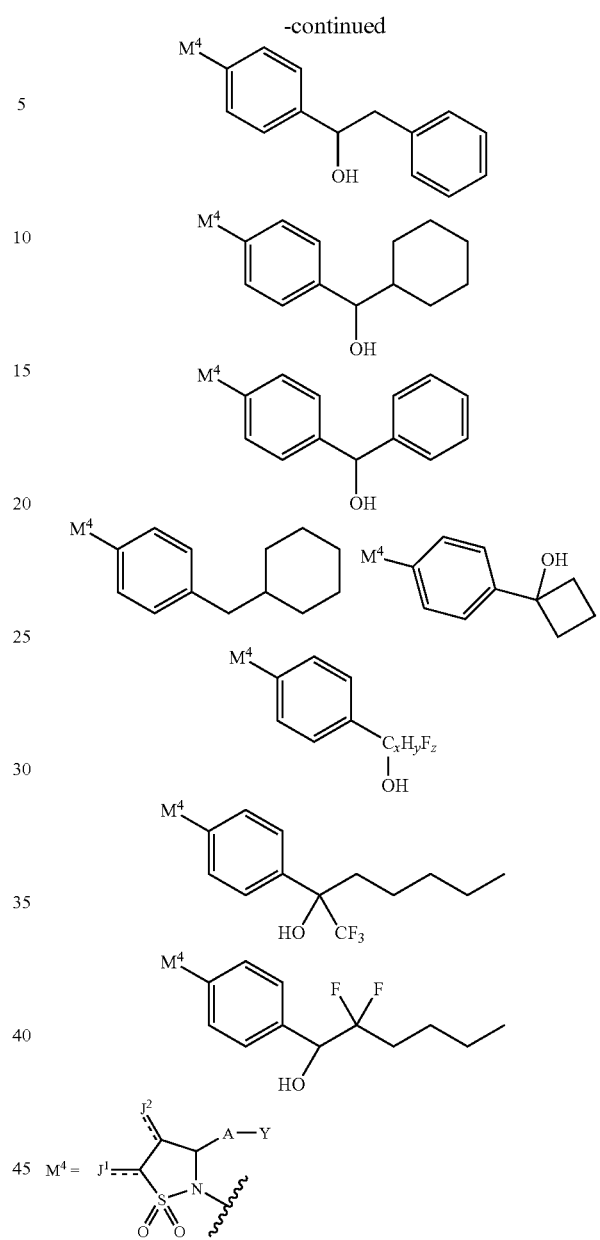
In the above embodiments, x is 5, 6, or 7, and y+z is 2x+1.
In one embodiment, x is 5 and y+z is 11.
In another embodiment, x is 6 and y+z is 13.
In another embodiment, x is 7 and y+z is 15.
Hypothetical examples of useful compounds are shown below.
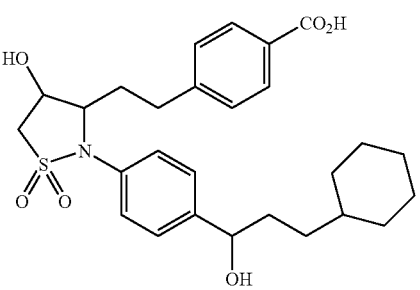

-continued
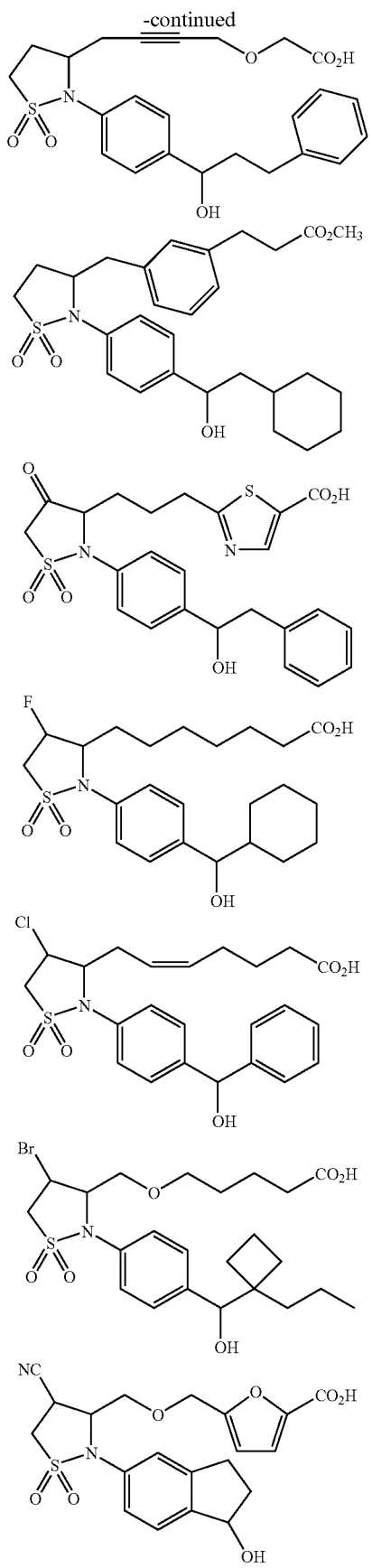
-continued
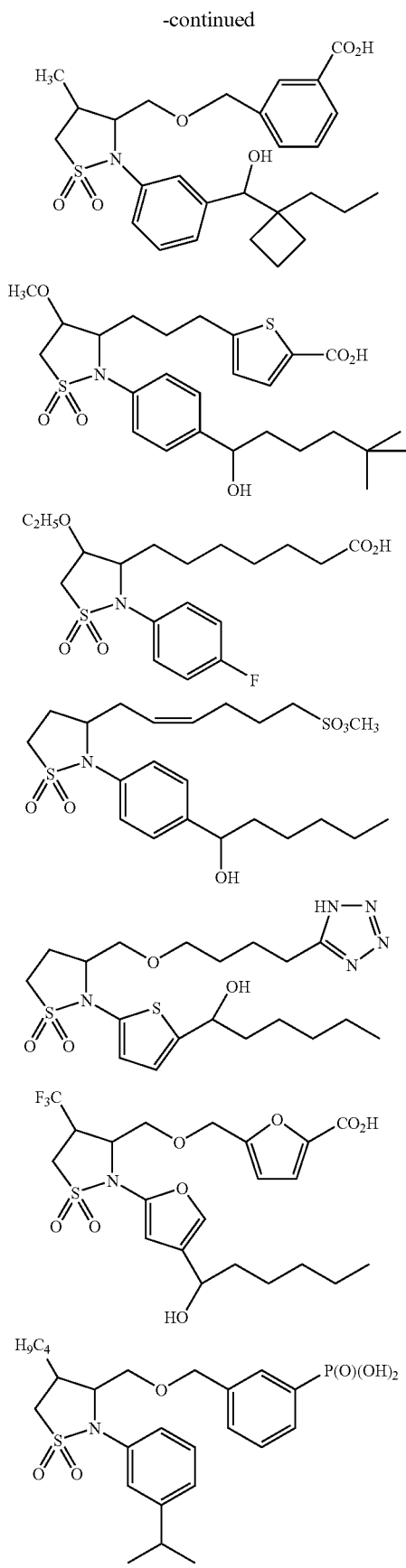

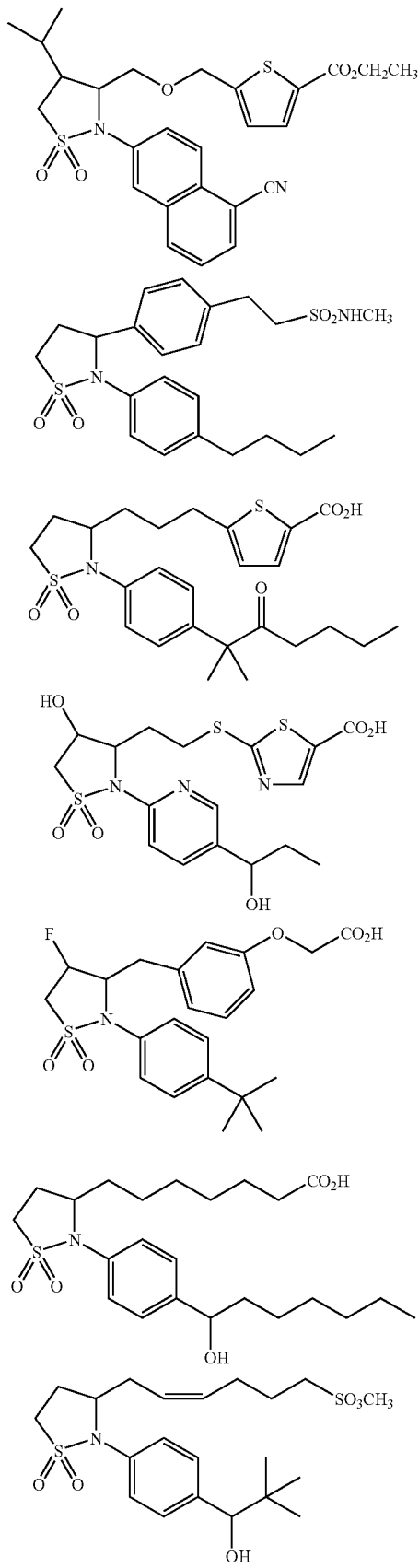
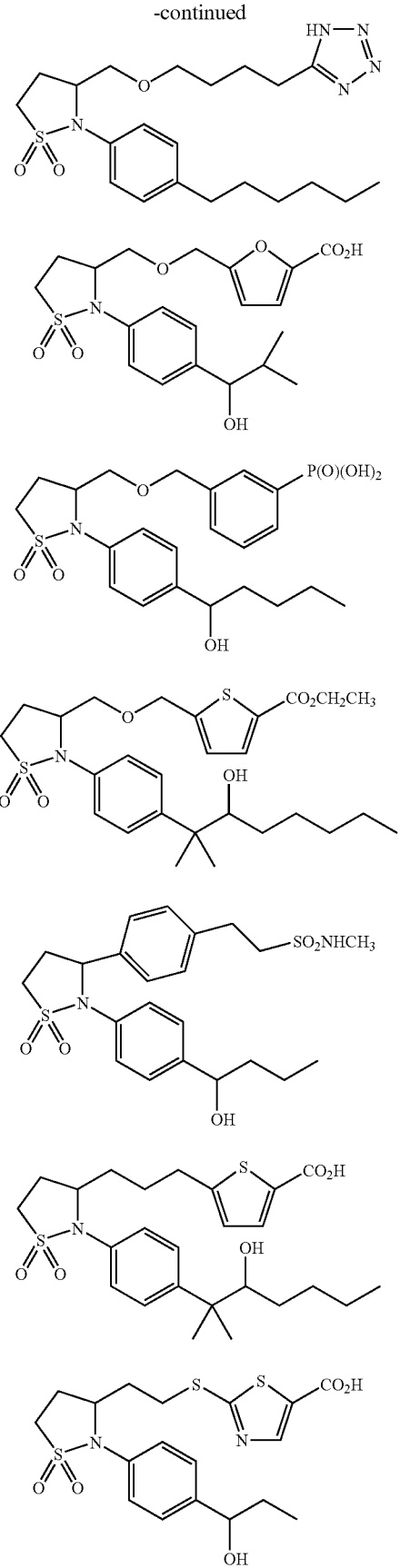

-continued

COMPOUND EXAMPLES

The following are hypothetical examples of useful compounds:

Compound Example 1

A compound having a structure or a pharmaceutically acceptable salt thereof, or a prodrug thereof;

wherein a dashed line represents the presence or absence of a bond;

Y is an organic acid functional group, or an amide or ester thereof comprising up to 14 carbon atoms; or Y is hydroxymethyl or an ether thereof comprising up to 14 carbon atoms; or Y is a tetrazolyl functional group;

A is $-(CH_2)_6-$, cis $-CH_2CH=CH-(CH_2)_3-$, or $-CH_2C\equiv C-(CH_2)_3-$, wherein 1 or 2 carbon atoms may be replaced by S or O; A is $-(CH_2)_m-Ar-(CH_2)_o-$ wherein Ar is interarylene or heterointerarylene, the sum of m and o is 1, 2, 3, or 4, and wherein one $CH_2$ may be replaced by S or O;

$J^1$ and $J^2$ are independently H; O; OH; O-alkyl having 1, 2, 3, 4, 5 or 6 carbon atoms; alkyl having 1, 2, 3, 4, 5, or 6 carbon atoms;

F; Cl; Br; I; CN; or $CF_3$; and

B is substituted aryl or substituted heteroaryl.

Compound Example 2

The compound according to compound example 1 wherein Y is selected from $CO_2R^2$, $CON(R^2)_2$, $CON(OR^2)R^2$, $CON(CH_2CH_2OH)_2$, $CONH(CH_2CH_2OH)$, $CH_2OH$, $P(O)(OH)_2$, $CONHSO_2R^2$, $SO_2N(R^2)_2$, $SO_2NHR^2$, and wherein $R^2$ is independently H, $C_1$-$C_6$ alkyl, unsubstituted phenyl, or unsubstituted biphenyl.

Compound Example 3

The compound according to compound example 1 or 2 wherein B is substituted phenyl.

Compound Example 4

The compound according to compound example 1 or 2 having a structure or a pharmaceutically acceptable salt thereof, or a prodrug thereof;
wherein R is hydrogen or $C_{1-10}$ hydrocarbyl.

Compound Example 5

The compound according to compound example 4 wherein R is alkyl.

Compound Example 6

The compound according to compound example 4 wherein R is arylalkyl.

Compound Example 7

The compound according to compound example any one of compound examples 1 to 6 having a structure or a pharmaceutically acceptable salt thereof, or a prodrug thereof;
wherein R is hydrogen or $C_{1-10}$ hydrocarbyl.

Compound Example 8

The compound according to compound example 1 or 2 wherein A is (3-methylphenoxy)methyl.

Compound Example 9

The compound according to compound example 1 or 2 wherein A is (4-but-2-ynyloxy)methyl.

Compound Example 10

The compound according to compound example 1 or 2 wherein A is 2-(2-ethylthio)thiazol-4-yl.

Compound Example 11

The compound according to compound example 1 or 2 wherein A is 2-(3-propyl)thiazol-5-yl.

Compound Example 12

The compound according to compound example 1 or 2 wherein A is 3-methoxymethyl)phenyl.

Compound Example 13

The compound according to compound example 1 or 2 wherein A is 3-(3-propylphenyl.

Compound Example 14

The compound according to compound example 1 or 2 wherein A is 3-methylphenethyl.

Compound Example 15

The compound according to compound example 1 or 2 wherein A is 4-(2-ethyl)phenyl.

Compound Example 16

The compound according to compound example 1 or 2 wherein A is 4-phenethyl.

Compound Example 17

The compound according to compound example 1 or 2 wherein A is 4-methoxybutyl.

Compound Example 18

The compound according to compound example 1 or 2 wherein A is 5-(methoxymethyl)furan-2-yl.

Compound Example 19

The compound according to compound example 1 or 2 wherein A is 5-(methoxymethyl)thiophen-2-yl.

Compound Example 20

The compound according to compound example 1 or 2 wherein A is 5-(3-propyl)furan-2-yl.

Compound Example 21

The compound according to compound example 1 or 2 wherein A is 5-(3-propyl)thiophen-2-yl.

Compound Example 22

The compound according to compound example 1 or 2 wherein A is 6-hexyl.

Compound Example 23

The compound according to compound example 1 or 2 wherein A is (Z)-6-hex-4-enyl.

Compound Example 24

The compound according to any one of compound examples 1, 2, and 8-23 wherein B is 4-(1-hydroxy-2,2-dimethylpropyl)phenyl.

Compound Example 25

The compound according to any one of compound examples 1, 2, and 8-23 wherein B is 4-(1-hydroxy-2-methylpropan-2-yl)phenyl.

Compound Example 26

The compound according to any one of compound examples 1, 2, and 8-23 wherein B is 4-(1-hydroxy-2-methylpropyl)phenyl.

Compound Example 27

The compound according to any one of compound examples 1, 2, and 8-23 wherein B is 4-(1-hydroxybutyl)phenyl.

Compound Example 28

The compound according to any one of compound examples 1, 2, and 8-23 wherein B is 4-(1-hydroxyheptyl)phenyl.

Compound Example 29

The compound according to any one of compound examples 1, 2, and 8-23 wherein B is 4-(1-hydroxyhexyl)phenyl.

Compound Example 30

The compound according to any one of compound examples 1, 2, and 8-23 wherein B is 4-(1-hydroxypentyl)phenyl.

Compound Example 31

The compound according to any one of compound examples 1, 2, and 8-23 wherein B is 4-(1-hydroxypropyl)phenyl.

Compound Example 32

The compound according to any one of compound examples 1, 2, and 8-23 wherein B is 4-(3-hydroxy-2-methylheptan-2-yl)phenyl.

Compound Example 33

The compound according to any one of compound examples 1, 2, and 8-23 wherein B is 4-(3-hydroxy-2-methyloctan-2-yl)phenyl.

Compound Example 34

The compound according to any one of compound examples 1, 2, and 8-23 wherein B is 1-hydroxy-2,3-dihydro-1H-inden-5-yl.

Compound Example 35

The compound according to any one of compound examples 1, 2, and 8-23 wherein B is 2,3-dihydro-1H-inden-5-yl.

Compound Example 36

The compound according to any one of compound examples 1, 2, and 8-23 wherein B is 3-(hydroxy(1-propyl-cyclobutyl)methyl)phenyl.

Compound Example 37

The compound according to any one of compound examples 1, 2, and 8-23 wherein B is 4-(1-hydroxy-5,5-dimethylhexyl)phenyl.

Compound Example 38

The compound according to any one of compound examples 1, 2, and 8-23 wherein B is 4-(hydroxy(1-propyl-cyclobutyl)methyl)phenyl.

Compound Example 39

The compound according to any one of compound examples 1, 2, and 8-23 wherein B is 4-tert-butylphenyl.

Compound Example 40

The compound according to any one of compound examples 1, 2, and 8-23 wherein B is 4-hexylphenyl.

Compound Example 41

The compound according to any one of compound examples 1, 2, and 8-23 wherein B is 4-(1-hydroxy-2-phenylethyl)phenyl.

Compound Example 42

The compound according to any one of compound examples 1, 2, and 8-23 wherein B is 4-(1-hydroxy-3-phenylpropyl)phenyl.

Compound Example 43

The compound according to any one of compound examples 1, 2, and 8-23 wherein B is 4-(1-hydroxycyclobutyl)phenyl.

Compound Example 44

The compound according to any one of compound examples 1, 2, and 8-23 wherein B is 4-(2-cyclohexyl-1-hydroxyethyl)phenyl.

Compound Example 45

The compound according to any one of compound examples 1, 2, and 8-23 wherein B is 4-(3-cyclohexyl-1-hydroxypropyl)phenyl.

Compound Example 46

The compound according to any one of compound examples 1, 2, and 8-23 wherein B is 4-(cyclohexyl(hydroxy)methyl)phenyl.

Compound Example 47

The compound according to any one of compound examples 1, 2, and 8-23 wherein B is 4-(cyclohexylmethyl)phenyl.

Compound Example 48

The compound according to any one of compound examples 1, 2, and 8-23 wherein B is 4-(hydroxy(phenyl)methyl)phenyl.

Compound Example 49

The compound according to any one of compound examples 1 to 48 wherein $J^1$ is H.

Compound Example 50

The compound according to any one of compound examples 1 to 48 wherein $J^1$ is O.

Compound Example 51

The compound according to any one of compound examples 1 to 48 wherein $J^1$ is OH.

Compound Example 52

The compound according to any one of compound examples 1 to 48 wherein $J^1$ is O-alkyl having 1, 2, 3, 4, 5 or 6 carbon atoms.

Compound Example 53

The compound according to any one of compound examples 1 to 48 wherein $J^1$ is alkyl having 1, 2, 3, 4, 5, or 6 carbon atoms.

Compound Example 54

The compound according to any one of compound examples 1 to 48 wherein $J^1$ is F.

Compound Example 55

The compound according to any one of compound examples 1 to 48 wherein $J^1$ is Cl.

Compound Example 56

The compound according to any one of compound examples 1 to 48 wherein $J^1$ is Br.

Compound Example 57

The compound according to any one of compound examples 1 to 48 wherein $J^1$ is I.

Compound Example 58

The compound according to any one of compound examples 1 to 48 wherein $J^1$ is CN.

Compound Example 59

The compound according to any one of compound examples 1 to 48 wherein $J^1$ is $CF_3$.

Compound Example 60

The compound according to any one of compound examples 1 to 59 wherein $J^2$ is H.

Compound Example 61

The compound according to any one of compound examples 1 to 59 wherein $J^2$ is O.

Compound Example 62

The compound according to any one of compound examples 1 to 59 wherein $J^2$ is OH.

Compound Example 63

The compound according to any one of compound examples 1 to 59 wherein $J^2$ is O-alkyl having 1, 2, 3, 4, 5 or 6 carbon atoms.

Compound Example 64

The compound according to any one of compound examples 1 to 59 wherein $J^2$ is alkyl having 1, 2, 3, 4, 5, or 6 carbon atoms.

Compound Example 65

The compound according to any one of compound examples 1 to 59 wherein $J^2$ is F.

Compound Example 66

The compound according to any one of compound examples 1 to 59 wherein $J^2$ is Cl.

Compound Example 67

The compound according to any one of compound examples 1 to 59 wherein $J^2$ is Br.

Compound Example 68

The compound according to any one of compound examples 1 to 59 wherein $J^2$ is I.

Compound Example 69

The compound according to any one of compound examples 1 to 59 wherein $J^2$ is CN.

Compound Example 70

The compound according to any one of compound examples 1 to 59 wherein $J^2$ is $CF_3$.

The following are hypothetical examples of compositions, kits, methods, uses, and medicaments employing the hypothetical compound examples.

Composition Example

A composition comprising a compound according to any one of compound examples 1 to 70, wherein said composition is a liquid which is ophthalmically acceptable.

Medicament Examples

Use of a compound according to any one of compound examples 1 to 70 in the manufacture of a medicament for the treatment of glaucoma or ocular hypertension in a mammal.

Use of a compound according to any one of compound examples 1 to 70 in the manufacture of a medicament for the treatment of baldness in a person.

A medicament comprising a compound according to any one of compound examples 1 to 70, wherein said composition is a liquid which is ophthalmically acceptable.

Method Example

A method comprising administering a compound according to any one of compound examples 1 to 70 to a mammal for the treatment of glaucoma or ocular hypertension.

Kit Example

A kit comprising a composition comprising compound according to any one of compound examples 1 to 70, a container, and instructions for administration of said composition to a mammal for the treatment of glaucoma or ocular hypertension.

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted. Ester prodrugs of the compounds disclosed herein are specifically contemplated. An ester may be derived from a carboxylic acid of Cl (i.e. the terminal carboxylic acid of a natural prostaglandin), or an ester may be derived from a carboxylic acid functional group on another part of the molecule, such as on a phenyl ring. While not intending to be limiting, an ester may be an alkyl ester, an aryl ester, or a heteroaryl ester. The term alkyl has the meaning generally understood by those skilled in the art and refers to linear, branched, or cyclic alkyl moieties. $C_{1-6}$ alkyl esters are particularly useful, where alkyl part of the ester has from 1 to 6 carbon a includes, but is not limited to, methyl, ethyl, propyl, isopropyl, n-butyl, sec-butyl, iso-butyl, t-butyl, pentyl isomers, hexyl isomers, cyclopropyl, cyclobutyl, cyclopentyl, cyclohexyl, and combinations thereof having from 1-6 carbon atoms, etc.

Those skilled in the art will readily understand that for administration or the manufacture of medicaments the compounds disclosed herein can be admixed with pharmaceutically acceptable excipients which per se are well known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the presently useful compound or compounds may be in the range of about 0.5 or about 1 to about 100 mg/kg/day.

A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

The actual dose of the active compounds of the present invention depends on the specific compound, and on the condition to be treated; the selection of the appropriate dose is well within the knowledge of the skilled artisan.

For treatment of diseases affecting the eye including glaucoma, these compounds can be administered topically, periocularly, intraocularly, or by any other effective means known in the art.

Biological Results

| Compound | EP2 | | | | | EP4 | | | |
|---|---|---|---|---|---|---|---|---|---|
| | cAMP EC50 (nM) | % PGE2 | Ca2+ signal EC50 (nM) | % Inh | Binding EC50 (nM) | % PGE2 | Ca2+ signal EC50 (nM) | % Inh | Binding EC50 (nM) |
| 15 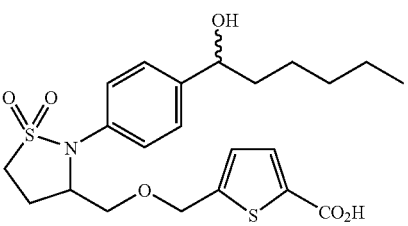 | 115 | | 8316 | | 2920 | | NA | | NA |
| 17 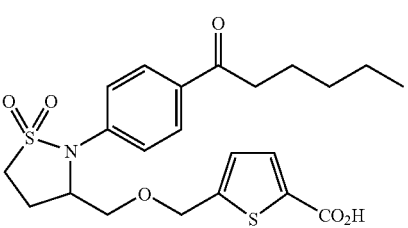 | 98 | | 5425 | | 1201 | | NA | | NA |

These compounds may be prepared by a number of methods known in the art. For example, PCT Application No PCT/US2006/007797, filed on Mar. 6, 2006, which claims priority to U.S. Provision Patent Application No. 60/660,748, filed on Mar. 10, 2005, both of which expressly incorporated herein by reference; and U.S. Pat. No. 4,087,435, which is expressly incorporated herein by reference, may be adapted to prepare the compounds disclosed herein. Schemes 1 and 2 show a typical example of a method of preparing these compounds using methods adapted from these references. Other methods are apparent to those of ordinary skill in the art.

Scheme 1

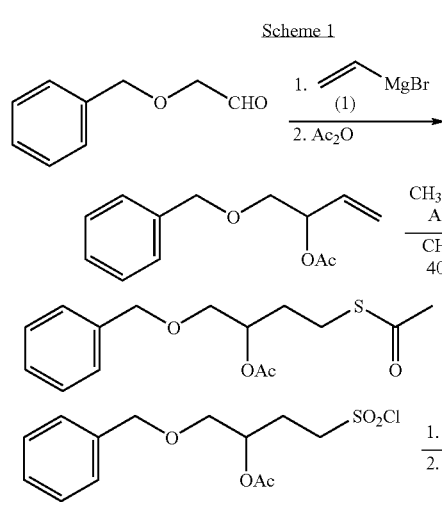

-continued

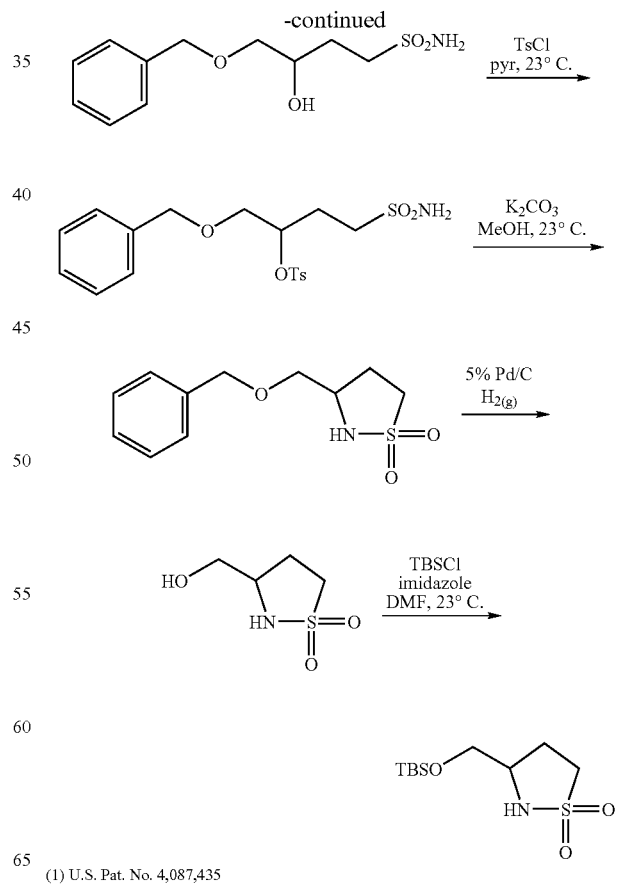

(1) U.S. Pat. No. 4,087,435

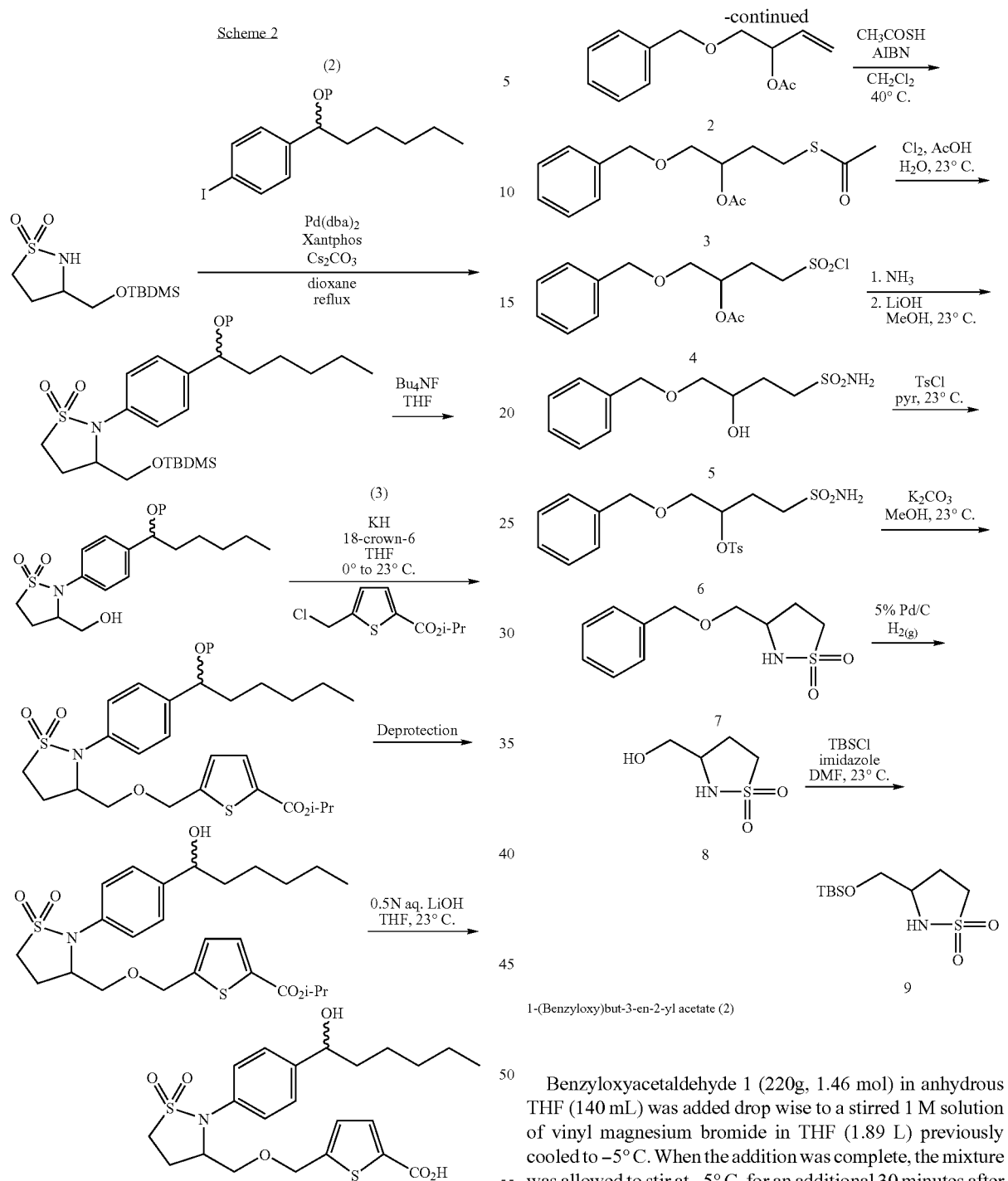

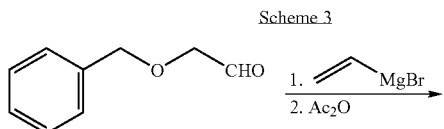

1-(Benzyloxy)but-3-en-2-yl acetate (2)

Benzyloxyacetaldehyde 1 (220g, 1.46 mol) in anhydrous THF (140 mL) was added drop wise to a stirred 1 M solution of vinyl magnesium bromide in THF (1.89 L) previously cooled to −5° C. When the addition was complete, the mixture was allowed to stir at −5° C. for an additional 30 minutes after which time TLC analysis showed a complete reaction. Acetic anhydride (222 mL, 240 g, 2.35 mol, 1.6 eq) was then added and the mixture allowed to slowly warm-up to room temperature overnight. Iced water (1 L) was then added to the reaction followed by EtOAc (700 mL) and the mixture stirred for 10 min. The layers were separated and the aqueous layer extracted with EtOAc (700 mL). The combined organics were washed with brine (700 mL), dried (MgSO$_4$) and concentrated in vacuo to give the crude product as an orange oil. Purification through a silica pad afforded the acetate 2 as a yellow oil (309 g, 97%).

4-(Acetylthio)-1-(benzyloxy)butan-2-yl acetate (3)

The acetate 2 (44.5 g, 0.202 mol) was taken up in toluene (450 ml) and warmed to 90° C. with stirring under nitrogen. AIBN (3.32 g, 20.2 mmol, 0.1 eq.) was added. A solution of thioacetic acid (16.91 g, 0.22 mol, 1.1 eq.) in toluene (450 ml) was then added over 3 hours. After each quarter of the solution was added additional AIBN (0.83 g, 5.06 mmol) was added to the reaction. The reaction mixture was heated at 90° C. for an additional 19 hours after which time a small sample was removed and concentrated for NMR analysis. This showed that the ratio of product to starting material as approximately 7:1. In an attempt to drive the reaction to go to completion, extra thioacetic acid (3.0 g, 0.2 eq.) in toluene (80 ml) and AIBN (0.83 g) was added. The reaction was heated to 90° C. for a second night then examined by NMR, which showed no further progress. The reaction mixture was cooled, washed with saturated aqueous sodium bicarbonate solution (2×400 ml), water (300 ml) then concentrated in vacuo.

The crude concentrated reaction mixture (123 g) was dissolved in dichloromethane (0.8 L) then mixed carefully with saturated aqueous sodium bicarbonate solution (0.8 L) in a 3 L flask. After 1 hour of stirring, the layers were separated and the organic layer stirred again with fresh saturated aqueous sodium bicarbonate solution (0.8 L). After stirring for 30 minutes the layers were separated and the organic layer concentrated. Purification by flash chromatography (silica gel, heptane/ethyl acetate (9:1) afforded 42 g (70%) of thioacetate 3 as a pale yellow oil.

1-(Benzyloxy)-4-(chlorosulfonyl) butan-2-yl acetate (4)

In a 3 L flange flask was dissolved thioacetate 3 (170 g, 0.57 mol) in 80% acetic acid (1530 mol) giving an orange solution. This was cooled using an ice bath to an internal temperature of 10° C. before chlorine is slowly bubbled through the solution. The reaction was exothermic and the chlorine flow was adjusted to maintain an internal temperature below 25° C. After 3 hours, the resultant green solution was checked (NMR) to ensure complete consumption of starting material had occurred and that product had formed. The reaction was then poured into water (10 vole, 1.7 L) and formed a white emulsion. The mixture was extracted with MTBE (2×1.7 L, 2×10 vol). The combined organics were washed with brine (1.7 L) then dried (MgSO$_4$), filtered and evaporated to give the sulfonyl chloride 4 as an orange oil (155.1 g).

4-(Benzyloxy)-3-hydroxybutane-1-sulfonamide (5)

Sulfonyl chloride 4 (155.1 g) was added slowly to liquid ammonia (−78° C., 250 mL) over 30 minutes. The resultant orange solution was slowly warmed to room temperature and stirred over a weekend. After this time, the thick brown oil was diluted with DCM (2 vol, 310 mL) and filtered to remove ammonium chloride (13g of expected 26g). The filtrate was evaporated to give an orange oil.

The resultant oil was taken up in methanol (10 vol, 1.6 L) and was stirred at 18° C. To this was added LiOH (13.89 g, 0.58 mol) over 5 minutes with stirring. The reaction warmed during the addition to 24° C. and was left stirring overnight at ambient temperature. The mixture was concentrated under reduced pressure, was diluted with water (500 mL) and was extracted with iPrOAc (5×1 L). The combined extracts were evaporated to yield 64 g of impure 5. The aqueous was then extracted with DCM (5×1 L) to afford an additional 50 g of impure 5. The solids were combined and slurred in MTBE (220 mL) to give an off-white suspension that was filtered. The desired hydroxyl-sulfonamide 5 was obtained (55 g) after drying. The aqueous layer was reduced in volume to 50 mL at which point a white solid was seen to precipitate. This was filtered and dried under vacuum to give a further batch of 5 (27 g). The two solids were combined to give 82 g (60%) of pure hydroxyl-sulfonamide 5.

1-(Benzyloxy)-4-sulfamoylbutan-2-yl 4-methylbenzenesulfonate (6)

A solution of hydroxyl-sulfonamide 5 (77 g, 0.30 mol) in pyridine (730 mL, 9.5 vol) was cooled to <10° C. in a 2 L round bottom flask. Tosyl chloride (56.6 g, 0.30 mol) is added to the solution over 5 minutes maintaining the internal temperature below 10° C. The reaction was allowed to warm to room temperature with stirring overnight. The completed reaction was poured into water (10 vol, 770 mL) to give an orange solution which was extracted with iPrOAc/MTBE (1:1, 2×1.5L). The combined organics were washed with brine (2×500 mL), aqueous HCL (2M, 2×500 mL) then brine (1×500 mL). The organic portion was dried (Na$_2$SO$_4$), filtered and evaporated to give sulfonate 6 as an orange oil (78 g).

3-(Benzyloxymethyl)-isothiazolidine 1,1-dioxide (7)

Sulfonamide 6 (109 g, 0.26 mol) was dissolved in DMF (800 mL) and stirred at ambient temperature. To this was added K$_2$CO$_3$ (63 g, 0.46 mol) in one portion and the resultant mixture heated at reflux (oil bath 160° C.) for 3 hours. After this time the heating was ceased and the reaction allowed to cool with stirring overnight. The completed reaction was poured into water (1 L) and acidified with aqueous HCl (1M, ~500 mL) to pH 2. The resultant brown suspension was extracted with DCM (5×500 mL) and the combined organics washed with brine (1 L). A thick emulsion formed which was separated by the addition of iPrOAc until two distinct layers were visible. The organics were separated, dried (MgSO$_4$) and evaporated to give an orange oil (66 g). This oil was purified by flash column chromatography (silica gel, 5% MeOH/DCM) to yield dioxide 7 as a yellow-orange oil (40g, 64%).

3-(Hydroxymethyl)-isothiazolidine 1,1-dioxide (8)

Dioxide 7 (40 g, 0.17 mol) was placed in the glass liner within a 2 L Parr hydrogenator and dissolved in a mixture of IMS (150 ml) and iPrOAc (150 ml). A suspension of 5% palladium on carbon (Johnson Matthey type 392, 18 g) in iPrOAc (50 mL) was added and the suspension stirred under a hydrogen atmosphere of 70 psi for 3 days. After this time an NMR IPC was carried out that showed approx 15% benzylated material still present. After a further 4 days the reaction was 94% complete and it was decided to stop the hydrogenolysis. The palladium catalyst was filtered under nitrogen on a bed of celite, which was subsequently washed with IMS (250 mL) and iPrOAc (250 mL). The filtrate and washings were concentrated to give the crude product as an oil (26.26 g). The oil was purified by flash column chromatography (silica gel, DCM/methanol (9:1)) yielding 16.65 g (67%) of the hydroxyl-dioxide 8 as a white solid.

3-(tert-Butyldiphenylsilanyloxymethyl)-isothiazolidine 1,1-dioxide (9)

Hydroxy-dioxide 8 (16.65 g, 0.110 mol) was taken up in dry DCM (200 ml) and DMF (40 mL) and the resultant solution was chilled to 0° C. with stirring under nitrogen. Imidazole (8.25 g, 0.121 mol, 1.1 eq.) was added to the solution followed by TBS-chloride (18.26 g, 0.121 mol). After 2.5 hours the reaction was complete and water (250 ml) was added to the reaction mixture with rapid stirring. The layers were separated and the aqueous layer was extracted with DCM (250 ml). The combined organic extracts were dried over $MgSO_4$ and concentrated using a high vacuum rotary evaporator in an effort to remove residual DMF. The crude product (26 g) was then purified by flash chromatography (silica gel) eluting the column with DCM to remove the residual DMF. Collected fractions were combined and concentrated to give pure TDDMS-ether 9 as a very viscous clear oil (21.56 g, 74%).

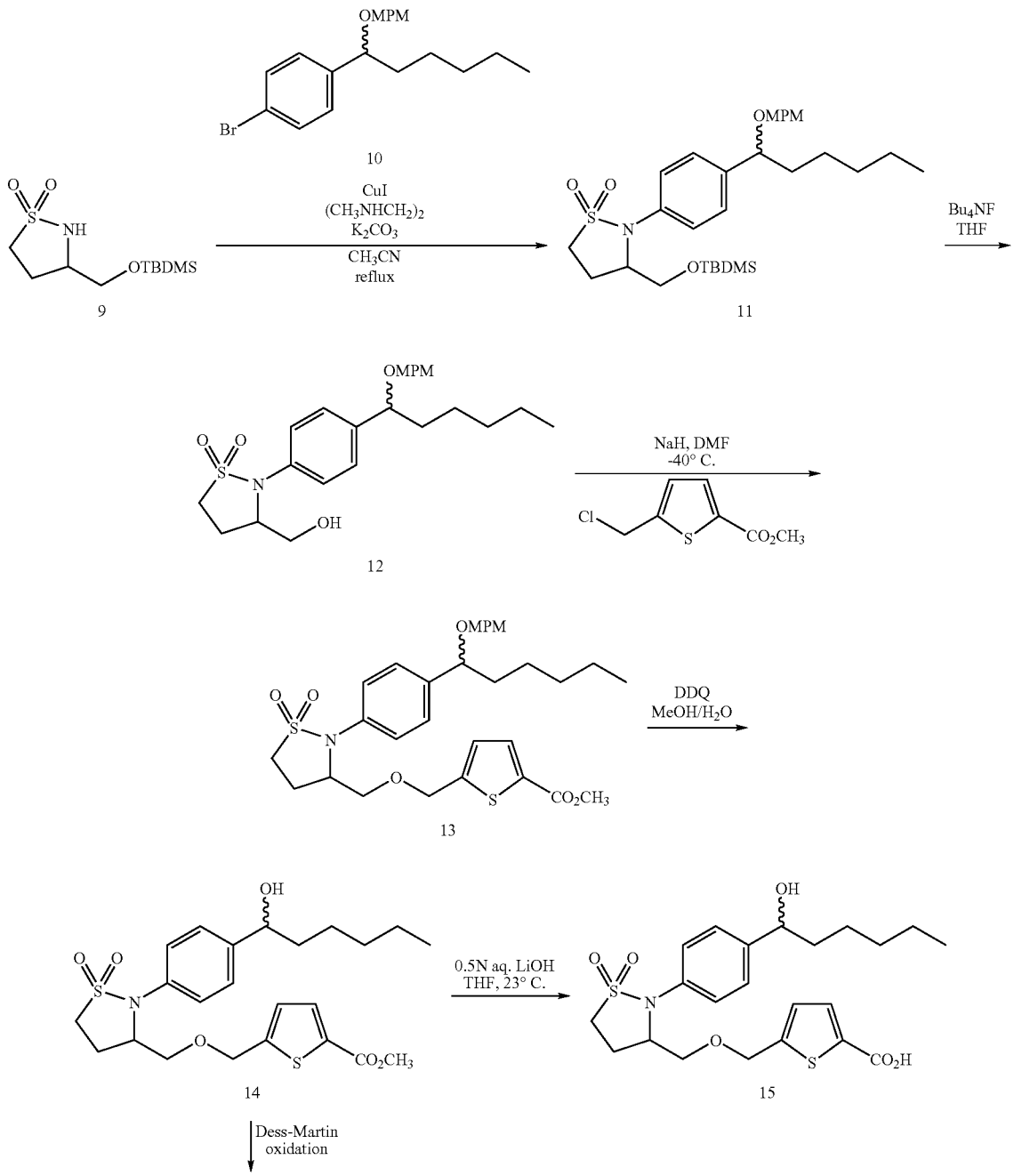

Scheme 4

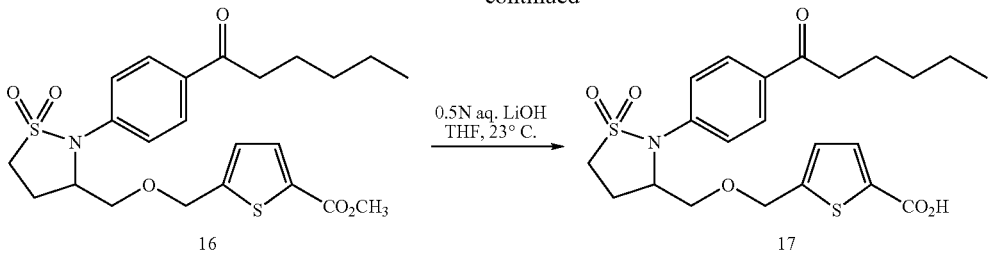

3-({[tert-Butyl(dimethyl)silyl]oxy}methyl)-2-(4-{1-[(4-methoxybenzyl)oxy]hexyl}phenyl)isothiothiazoline 1,1-dioxide (11)

Copper(I) iodide (82 mg, 0.43 mmol), N,N'-dimethylethyleneamine (51 μL, 0.43 mmol) and potassium carbonate (1.32 g, 9.65 mmol) were added sequentially to a solution of the dioxide 9 (1.27 g, 4.78 mmol) and aryl bromide 10 (1.8 g, 4.78 mmol) in acetonitrile (4 mL). The resultant mixture was degassed, purged under an atmosphere of nitrogen and then heated at 80° C. for 16 h. The mixture was cooled to room temperature, filtered and the filtrate concentrated in vacuo. Purification of the residue by flash column chromatography (silica gel, 3:1 hex/EtOAc) afforded 995 mg (46%) of the N-aryl dioxide 11.

2-(4-{1-[(4-Methoxybenzyl)oxy]hexyl}phenyl)isothiazolidin-3-ol 1,1-dioxide (12)

Tetrabutylammonium fluoride (2.6 mL of a 1.0 M solution in THF, 2.66 mmol) was added to a solution of the silyl ether 11 (995 mg, 1.77 mmol) in THF (20 mL) at 23° C. After stirring for 16 h the reaction was diluted with EtOAc and washed with $H_2O$ followed by brine. The organic portion was dried ($MgSO_4$), filtered and concentrated in vacuo. Purification of the residue by flash column chromatography (silica gel, 3:1 EtOAc/hex) gave 573 mg (72%) of the alcohol 12.

Methyl 5-({[2-(4-{1-(4-methoxybenyl)oxy]hexyl}phenyl)-1,1-dioxidoisothiazolidin-3-yl]oxy}methyl]thiophene-2-carboxylate (13)

Sodium hydride (10 mg, 0.39 mmol) was added to a solution of the alcohol 12 (117 mg, 0.26 mmol) in DMF (2 mL) at −40° C. After 15 minutes methyl 5-(chloromethyl)-2-thiophenecarboxylate (75 mg, 0.39 mmol) was added and the reaction was allowed to warm to room temperature on its own accord. After 16 h the reaction was diluted with EtOAc and washed with $H_2O$, saturated aqueous $NaHCO_3$ then brine. The organic portion was dried ($MgSO_4$), filtered and concentrated in vacuo. Purification of the residue by flash column chromatography (silica gel, 2:3 EtOAc/hex) yielded 76 mg (34%) of the methyl ester 13.

Methyl 5-[({2-[4-(1-hydroxyhexyl)phenyl]-1,1-dioxidoisothiazolidin-3-yl}oxy)methyl]thiophene-2-carboxylate (14)

2,3-Dichloro-5,6-dicyano-p-benzoquinone (33 mg, 0.145 mmol) was added to a mixture of the MPM-ether 13 (76 mg, 0.126 mmol) in $CHCl_3$ (1.5 mL) and $H_2O$ (0.1 mL) at 0° C. After 2 h the reaction was quenched by addition of saturated aqueous $NaHCO_3$ and then extracted with EtOAc. The organic portion was washed with saturated aqueous $NaHSO_3$ and brine then dried ($MgSO_4$), filtered and concentrated in vacuo. Purification of the residue by flash column chromatography (silica gel, 3:2 EtOAc/hex) afforded 61 mg (99%) of the alcohol 14.

5-[({2-[4-(1-Hydroxyhexyl)phenyl]-1,1-dioxidoisothiazolidin-3-yl}oxy)methyl]thiophene-2-carboxylate (15)

Lithium hydroxide (0.6 ml of a 0.5 N solution in $H_2O$, 0.29 mmol) was added to a solution of the ester 14 (61 mg, 0.127 mmol) in THF (1.2 mL) at 23° C. After 16 h the reaction was acidified with 10% citric acid and extracted with EtOAC. The organic portion was washed with brine (2×), dried ($Na_2SO_4$), filtered and concentrated in vacuo. Purification of the residue by flash column chromatography (silica gel, 9:1 $CH_2Cl_2$/MeOH) gave 51 mg (86%) of the free acid 15.

Methyl 5-({[2-(4-hexanoylphenyl)-1,1-dioxidoisothiazolidin-3-yl]oxy}methyl)thiophene-2-carboxylate (16)

1,1,1-Tris(acetyloxy)-1,1-dihydro-1,2-benziodoxol-3-(1H)-one (44 mg, 0.104 mmol) was added to a solution of the alcohol 14 (42 mg, 0.087 mmol) in $CH_2Cl_2$ (2 mL) at 23° C. After stirring for 16 h the reaction mixture with $CH_2Cl_2$ and filtered. The filtrate was concentrated in vacuo and purification of the residue by flash column chromatography (silica gel, 1:1 hex/EtOAc) gave 41 mg (98%) of the ketone 16.

5-({[2-(4-Hexanoylphenyl)-1,1-dioxidoisothiazolidin-3-yl]oxy}methyl)thiophene-2-carboxylate (17)

Lithium hydroxide (0.43 ml of a 0.5 N solution in $H_2O$, 0.216 mmol) was added to a solution of the ester 16 (45 mg, 0.094 mmol) in THF (0.86 mL) at 23° C. After 16 hours the reaction was acidified with 10% citric acid and extracted with EtOAC. The organic portion was washed with brine (2×), dried ($Na_2SO_4$), filtered and concentrated in vacuo. Purification of the residue by flash column chromatography (silica gel, 9:1 $CH_2Cl_2$/MeOH) gave 36 mg (82%) of the free acid 17.

A person of ordinary skill in the art understands the meaning of the stereochemistry associated with the hatched wedge/solid wedge structural features. For example, an introductory organic chemistry textbook (Francis A. Carey, Organic Chemistry, New York: McGraw-Hill Book Company 1987, p. 63) states "a wedge indicates a bond coming from the plane of the paper toward the viewer" and the hatched wedge, indicated as a "dashed line", "represents a bond receding from the viewer."

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the claims.

What is claimed is:

1. A compound represented by the formula

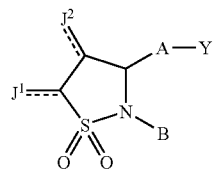

or a pharmaceutically acceptable salt thereof;
wherein a dashed line represents the presence or absence of a bond;
Y is selected from $CO_2R^2$, $CON(R^2)_2$, $CON(OR^2)R^2$, $CON(CH_2CH_2OH)_2$, $CONH(CH_2CH_2OH)$, $CH_2OH$, $P(O)(OH)_2$, $CONHSO_2R^2$, $SO_2N(R^2)_2$, $SO_2NHR^2$,

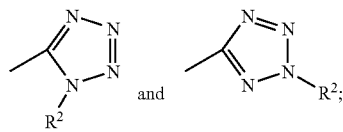

wherein $R^2$ is independently H, $C_1$-$C_6$ alkyl, unsubstituted phenyl, or unsubstituted biphenyl;
A is —$(CH_2)_6$—, cis —$CH_2CH{=}CH$—$(CH_2)_3$—, or —$CH_2C{\equiv}C$—$(CH_2)_3$—, wherein 1 or 2 carbon atoms may be replaced by S or O; or A is —$(CH_2)_m$—Ar—$(CH_2)_o$— wherein Ar is interarylene or heterointerarylene, the sum of m and o is 1, 2, 3, or 4, and wherein one $CH_2$ may be replaced by S or O;
$J^1$ and $J^2$ are independently H; O; OH; O-alkyl having 1, 2, 3, 4, 5 or 6 carbon atoms; alkyl having 1, 2, 3, 4, 5, or 6 carbon atoms; F; Cl; Br; I; CN; or $CF_3$; and
B is substituted aryl or substituted heteroaryl.

2. The compound of claim 1 wherein B is substituted phenyl.

3. The compound of claim 2 represented by the formula

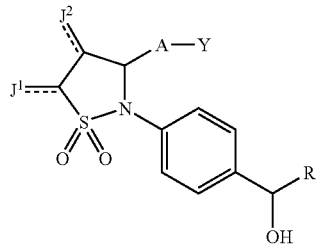

or a pharmaceutically acceptable salt thereof;
wherein R is hydrogen or $C_{1-10}$ hydrocarbyl.

4. The compound of claim 3 wherein R is alkyl.

5. The compound according to claim 1 wherein A is —$(CH_2)_m$—Ar—$(CH_2)_o$— wherein Ar is interarylene or heterointerarylene, the sum of m and o is 1, 2, 3, or 4, and wherein one $CH_2$ may be replaced by S or O.

6. The compound of claim 5 wherein A is —$(CH_2)_3Ar$—, —$O(CH_2)_2Ar$—, —$CH_2OCH_2Ar$—, —$(CH_2)_2OAr$, —$O(CH_2)_2Ar$—, —$CH_2OCH_2Ar$—, or —$(CH_2)_2OAr$, wherein Ar is monocyclic interheteroarylene.

7. The compound of claim 6 wherein Ar is interthienylene.

8. The compound of claim 6 wherein Ar is interthiazolylene.

9. The compound of claim 6 wherein Ar is interoxazolylene.

10. The compound of claim 1 wherein A is 6-hexyl.

11. The compound of claim 1 wherein A is (Z)-6-hex-4-enyl.

12. The compound of claim 1 wherein $J^1$ is H.

13. The compound of claim 1 wherein $J^2$ is H.

14. The compound of claim 1 wherein $J^2$ is O.

15. The compound of claim 1 wherein $J^2$ is OH.

16. The compound of claim 1 wherein $J^2$ is F.

17. The compound of claim 1 wherein $J^2$ is Cl.

18. The compound of claim 1 wherein $J^2$ is Br.

19. The compound of claim 1 wherein $J^2$ is CN.

20. The compound of claim 1 wherein $J^2$ is $CF_3$.

21. A composition comprising a compound according to any one of claims 1, and 6-20, wherein said composition is a liquid which is ophthalmically acceptable.

* * * * *

UNITED STATES PATENT AND TRADEMARK OFFICE
CERTIFICATE OF CORRECTION

PATENT NO. : 7,557,095 B2
APPLICATION NO. : 11/745317
DATED : July 7, 2009
INVENTOR(S) : Burk et al.

It is certified that error appears in the above-identified patent and that said Letters Patent is hereby corrected as shown below:

In column 1, line 32, delete "pupilary" and insert -- pupillary --, therefor.

In column 3, line 7, delete "bioisoteres" and insert -- bioisosteres --, therefor.

In column 5, line 57, delete "Phosponic" and insert -- Phosphonic --, therefor.

In column 10, line 2, delete "3,and" and insert -- 3, and --, therefor.

In column 11, line 28, delete "thiophene-2-yl." and insert -- thiophen-2-yl. --, therefor.

In column 13, line 7, delete "imidizololyl," and insert -- imidazolyl, --, therefor.

In column 15, line 32, delete ""C1-10"" and insert -- "$C_{1-10}$" --, therefor.

In column 25, line 20, delete "(3-propylphenyl." and insert -- (3-propylphenyl). --, therefor.

In column 30, line 57, after "carbon" delete "a" and insert -- atoms and --, therefor.

In column 37, line 5, delete "AlBN" and insert -- AIBN --, therefor.

In column 37, line 8, delete "AlBN" and insert -- AIBN --, therefor.

In column 37, line 15, delete "AlBN" and insert -- AIBN --, therefor.

In column 39, line 1, delete "3-(tert-Butyidiphenylsilanyloxymethyl)" and insert -- 3-(tert-Butyldiphenylsilanyloxymethyl) --, therefor.

In column 41, line 41, delete "(4-methoxybenyl)" and insert -- (4-methoxybenzyl) --, therefor.

In column 42, line 40, delete "mixture" and insert -- mixture was diluted --, therefor.

UNITED STATES PATENT AND TRADEMARK OFFICE
CERTIFICATE OF CORRECTION

PATENT NO.       : 7,557,095 B2
APPLICATION NO.  : 11/745317
DATED            : July 7, 2009
INVENTOR(S)      : Burk et al.

It is certified that error appears in the above-identified patent and that said Letters Patent is hereby corrected as shown below:

In column 44, line 22, in Claim 5, delete "$CH_2$may" and insert -- $CH_2$ may --, therefor.

In column 44, line 46, in Claim 21, delete "6-20," and insert -- 2-20, --, therefor.

Signed and Sealed this

Sixth Day of October, 2009

David J. Kappos
*Director of the United States Patent and Trademark Office*